(12) United States Patent
Jeon et al.

(10) Patent No.: US 10,211,265 B2
(45) Date of Patent: Feb. 19, 2019

(54) DISPLAY APPARATUS AND METHOD OF MANUFACTURING THE SAME

(71) Applicant: SAMSUNG DISPLAY CO., LTD., Yongin-si, Gyeonggi-do (KR)

(72) Inventors: Bogeon Jeon, Yongin-si (KR); Taeyoung Ahn, Yongin-si (KR); Sangwook Lee, Yongin-si (KR); Eunjeong Cho, Yongin-si (KR)

(73) Assignee: SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 105 days.

(21) Appl. No.: 15/372,427

(22) Filed: Dec. 8, 2016

(65) Prior Publication Data
US 2017/0278909 A1 Sep. 28, 2017

(30) Foreign Application Priority Data
Mar. 25, 2016 (KR) .......................... 10-2016-0036130

(51) Int. Cl.
*H01L 27/32* (2006.01)
*G06F 3/042* (2006.01)
(Continued)

(52) U.S. Cl.
CPC ........ *H01L 27/3227* (2013.01); *A61B 5/0077* (2013.01); *A61B 5/1171* (2016.02); *A61B 5/1172* (2013.01); *A61B 5/14552* (2013.01); *A61B 5/6898* (2013.01); *G06F 3/0421* (2013.01); *G06K 9/00013* (2013.01); *G06K 9/00067* (2013.01); *H01L 27/3248* (2013.01); *H01L 27/3262* (2013.01); *H01L 27/3272* (2013.01); *G06F 2203/04103* (2013.01); *G06K 2009/00932* (2013.01)

(58) Field of Classification Search
CPC ... A61B 5/1171; A61B 5/0077; A61B 5/1172; A61B 5/14552; A61B 5/6898; G06F 3/0421; G02F 1/13338; H01L 27/3227; H01L 27/3262; H01L 27/3248; H01L 27/3272; G06K 9/00013; G06K 9/00067
See application file for complete search history.

(56) References Cited

U.S. PATENT DOCUMENTS 8,963,817 B2 * 2/2015 Booth, Jr. ............ G09G 3/3208
345/39
9,389,715 B2 * 7/2016 Yi ......................... G06F 3/0412
(Continued)

FOREIGN PATENT DOCUMENTS

CN 103107172 A 5/2013

*Primary Examiner* — Sardis F Azongha
(74) *Attorney, Agent, or Firm* — Lee & Morse P.C.

(57) ABSTRACT

A display apparatus includes a first pixel, a second pixel, a light sensor, and a light shield. The first pixel has a first light-emitting device which includes a first emission layer that emits light in a first wavelength band in a first direction. The second pixel has a second light-emitting device which includes a second emission layer to emit light in a second wavelength band in a second direction different from the first direction. The second emission layer is below the first emission layer of the first light-emitting device. The light sensor senses light in the second wavelength band emitted from the second pixel and reflected by an object. The light shield is arranged along a light path incident to the light sensor.

24 Claims, 34 Drawing Sheets

(51) Int. Cl.
*G06K 9/00* (2006.01)
*A61B 5/1171* (2016.01)
*A61B 5/00* (2006.01)
*A61B 5/1172* (2016.01)
*A61B 5/1455* (2006.01)

(56) References Cited

U.S. PATENT DOCUMENTS

| | | | |
|---|---|---|---|
| 9,961,178 B2 * | 5/2018 | Hong | G06K 9/00013 |
| 2012/0146953 A1 * | 6/2012 | Yi | G06F 3/0412 |
| | | | 345/175 |
| 2012/0248452 A1 * | 10/2012 | Yeo | G06F 3/0412 |
| | | | 257/60 |
| 2013/0249817 A1 * | 9/2013 | Jung | G06F 3/0412 |
| | | | 345/173 |
| 2014/0036168 A1 * | 2/2014 | Ludwig | G06F 3/0412 |
| | | | 349/12 |
| 2014/0061617 A1 | 3/2014 | So et al. | |
| 2014/0306204 A1 * | 10/2014 | Niu | H01L 27/3267 |
| | | | 257/40 |
| 2015/0010215 A1 * | 1/2015 | Fukuda | G06K 9/00013 |
| | | | 382/115 |

* cited by examiner

| $I_{dark}$ | 7.94E−13 A |
| --- | --- |
| $I_{IR}$ | 7.12E−10 A |
| IR Sensitivity | 916.0 |
| IR Gain | 78.8 |

DISPLAY APPARATUS AND METHOD OF MANUFACTURING THE SAME

CROSS-REFERENCE TO RELATED APPLICATION

Korean Patent Application No. 10-2016-0036130, filed on Mar. 25, 2016, and entitled, "Display Apparatus and Method of Manufacturing the Same," is incorporated by reference herein in its entirety.

BACKGROUND

1. Field

One or more embodiments described herein relate to a display apparatus and a method of manufacturing a display apparatus.

2. Description of the Related Art

The demand for measuring or sensing biometric information is increasing. Biometric information may be measured or sensed using separate devices, one device for irradiating light onto a human body and another device for collecting light reflected from or transmitted in the human body.

SUMMARY

In accordance with one or more embodiments, a display apparatus includes a substrate; a first pixel on the substrate, the first pixel including a first light-emitting device to emit light in a first wavelength band in a first direction, the first light-emitting device including a first emission layer; a second pixel on the substrate, the second pixel including a second light-emitting device to emit light in a second wavelength band in a second direction different from the first direction, the second light-emitting device including a second emission layer below the first emission layer of the first light-emitting device; a light sensor on the substrate to sense light in the second wavelength band emitted from the second pixel and reflected by an object; and a light shield adjacent to the light sensor on the substrate.

The light sensor may include a thin film transistor and the thin film transistor may include a third semiconductor layer. The third semiconductor layer may include amorphous silicon germanium. The display apparatus may include an insulating layer between the light shield and the third semiconductor layer. The insulating layer may include at least one of silicon nitride or silicon oxide.

The light shield may have a stack structure including a first light shielding layer including amorphous germanium and a second light shielding layer including amorphous silicon germanium.

The first light emitting device may include the first emission layer between a first electrode and a second electrode, the first emission layer to emit light in the first wavelength band, and the second light emitting device includes the second emission layer between a first electrode and a second electrode, the second emission layer to emit light in the second wavelength band. The first electrode of the first light-emitting device may include a reflection electrode and the second electrode of the first light-emitting device includes a transparent electrode, and the first electrode of the second light-emitting device may include a transparent electrode and the second electrode of the second light-emitting device includes a reflection electrode. The second electrode of the second light-emitting device maybe on a same layer as the first electrode of the first light-emitting device.

The display device may include an insulating layer between the second electrode of the second light-emitting device and the first electrode of the first light-emitting device. The first pixel may include a first thin film transistor electrically connected to the first light-emitting device and including a first semiconductor layer, and the second pixel may include a second thin film transistor electrically connected to the second light-emitting device and including a second semiconductor layer.

Each of the first semiconductor layer and the second semiconductor layer may include polysilicon. A resolution of the second pixel may be lower than a resolution of the first pixel. The first wavelength band may include a visible light range and the second wavelength band may include an infrared range.

In accordance with one or more other embodiments, a method of manufacturing a display apparatus includes preparing a substrate; forming, on the substrate, a light sensor to sense light of a second wavelength band reflected by an object; forming, on the light sensor, a second light-emitting device to emit the light of the second wavelength band in a direction opposite to the substrate; forming, on the second light-emitting device, a first light-emitting device to emit light of a first wavelength band in a direction of the substrate; and forming a light shield in a path of light incident to the light sensor. A first electrode of the first light-emitting device and a second electrode of the second light-emitting device are concurrently formed.

Forming the light shield may include, before forming the light sensor, stacking a first light shielding layer and a second light shielding layer on the substrate and patterning the first light shielding layer and the second light shielding layer. Forming the light shield may be performed during forming of the light sensor, and forming the light sensor may include stacking a first light shielding layer, a second light shielding layer, an insulating layer, and a semiconductor layer on the substrate and patterning the first light shielding layer, the second light shielding layer, the insulating layer, and the semiconductor layer. The first light shielding layer and the second light shielding layer may be included in the light shield, and the semiconductor layer may be included in the light sensor.

The method may include, before forming the first light-emitting device and the second light-emitting device, forming a first thin film transistor electrically connected to the first light-emitting device and a second thin film transistor electrically connected to the second light-emitting device. Before forming the first light-emitting device, the method may include forming an insulating layer on the second light-emitting device. The first wavelength band may include a visible light range and the second wavelength band may include an IR range.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
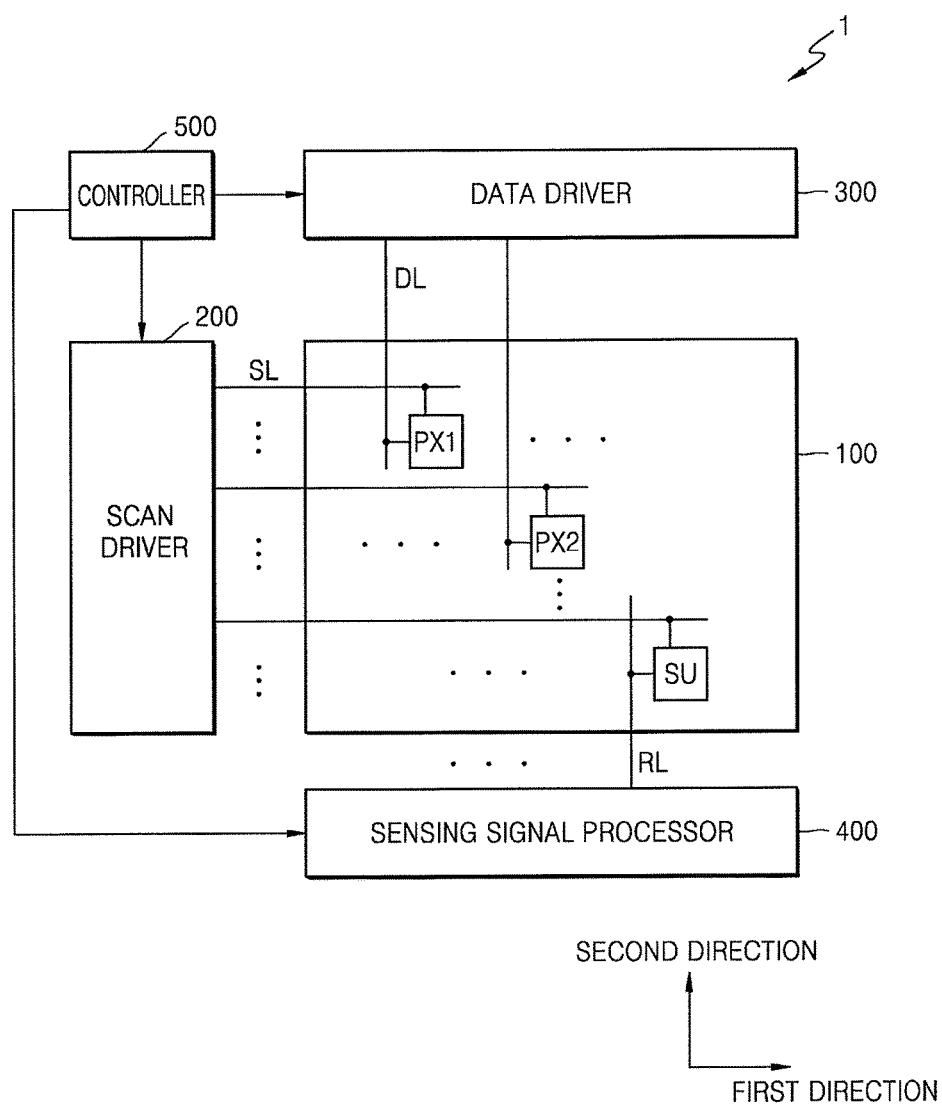
FIG. 1 illustrates an embodiment of a display apparatus.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. The embodiments may be combined to form additional embodiments.

In the drawings, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

When an element is referred to as being "connected" or "coupled" to another element, it can be directly connected or coupled to the another element or be indirectly connected or coupled to the another element with one or more intervening elements interposed therebetween. In addition, when an element is referred to as "including" a component, this indicates that the element may further include another component instead of excluding another component unless there is different disclosure.

Figure 2:
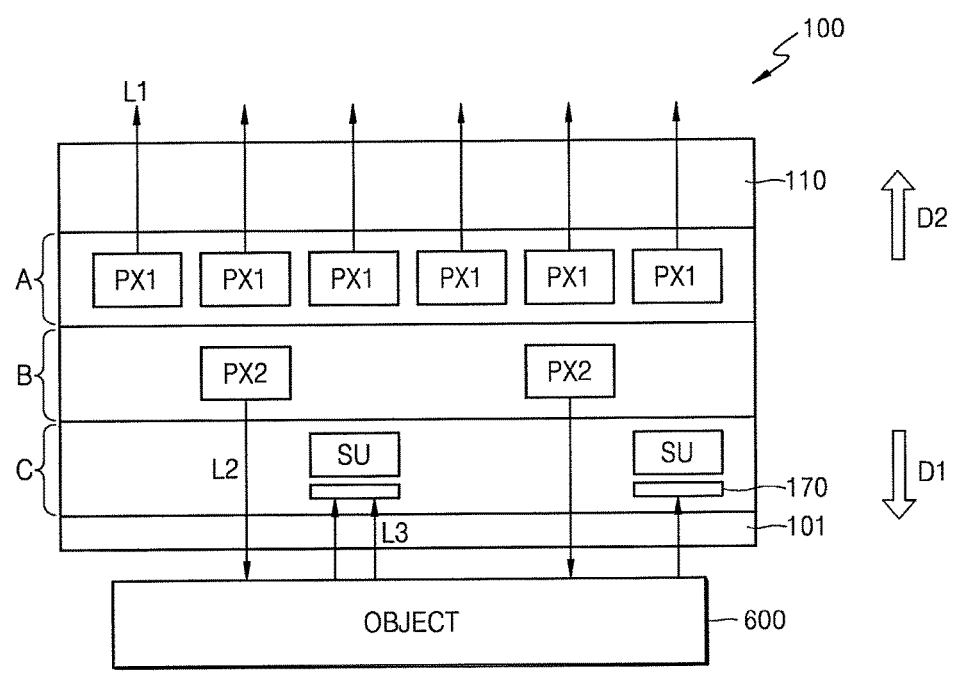
FIG. 2 illustrates an embodiment of a display panel.

FIG. 1 illustrates an embodiment of a display apparatus 1, and FIG. 2 illustrates an embodiment of a display panel 100 which, for example, may be included in the display apparatus 1, for sensing biometric information.

Referring to FIGS. 1 and 2, the display apparatus 1 may include the display panel 100, a scan driver 200, a data driver 300, a sensing signal processor 400, and a controller 500. The display panel 100 may include a display unit A, a light source unit B, a sensing unit C, and an encapsulation member 110 on the substrate 101 for encapsulating the substrate 101. The display panel 100 may be, for example, an encapsulation substrate coupled to the substrate 101 via an encapsulation material, or may be an encapsulation thin film having a structure in which an inorganic material and an organic material are alternately deposited on the substrate 101.

The display unit A, the light source unit B, and the sensing unit C may be in a display area of the substrate 101. The display unit A may include a plurality of first pixels PX1. The sensing unit C may include a plurality of sensor units SU. The light source unit B may include a plurality of second pixels PX2. The light source unit B may be arranged between the display unit A and the sensing unit C, as seen from a cross-sectional point of view.

In a display mode, the display apparatus 1 may display an image via light L1 emitted by the first pixels PX1 of the display unit A. Light L1 is emitted in a direction D2 opposite to that of the substrate 101. In a sensing mode, the display apparatus 1 may sense biometric information using the second pixels PX2 of the light source unit B and the sensor units SU of the sensing unit C. The display apparatus 1 may operate solely in the sensing mode or may operate in the sensing mode simultaneously with the display mode. The display apparatus 1 may operate in the sensing mode, for example, when a specific event is sensed, e.g., power on, object touch, etc.

In the sensing mode, when an object 600 contacts or comes close to the substrate 101, light L2 emitted from the second pixels PX2 of the light source unit B, in a direction D1 of the substrate 101, may be reflected (L3) by the object 600 and sensed by the sensor units SU. The object 600 may be, for example, a part of a human body, e.g., hand, finger, iris, etc. The display apparatus 1 may obtain biometric information based on a sensing signal from the sensor units SU. The display apparatus 1 may display the biometric information as an image using the first pixels PX1.

The substrate 101 has a display area including a plurality of scan lines SL extending in a first direction and a plurality of data lines DL and a plurality of read out lines RL extending in a second direction. These lines may be arranged apart from one another. Also, a plurality of power lines for applying a power voltage to the first pixels PX1 and the second pixels PX2 may be arranged in the display area.

The first pixels PX1 may be connected to the scan lines SL and the data lines DL and may emit the light L1 of a first wavelength band in the direction D2 opposite to (e.g., in a direction away from) the substrate 101. The first wavelength band may be, for example, in a visible light range of about 380 to about 750 nm. The first pixels PX1 may include a first color pixel emitting visible rays of a first color, a second color pixel emitting visible rays of a second color, and a third color pixel emitting visible rays of a third color. For example, the first color may be red, the second color may be green, and the third color may be blue. The first pixels PX1 may emit visible rays of a different combination of colors in another embodiment.

The second pixels PX2 may be connected to the scan lines SL and the data lines DL and may emit the light L2 of a second wavelength band in the direction D1 of the substrate 101. The second wavelength band may be, for example, in an infrared (IR) range including a near infrared (NIR) range of about 750 to about 1000 nm. The second pixels PX2 may include an IR pixel or an NIR pixel emitting infrared light. As illustrated in FIG. 2, the second pixels PX2 may be arranged below the first pixels PX1, as seen from a cross-sectional point of view.

The sensor units SU may be connected to the scan lines SL and the read out lines RL and may receive the reflection light L3, when the light L2 emitted from the second pixels PX2 is reflected from the object 600, which is in contact with or close to the substrate 101. The reflection light L3 may be light of the second wavelength band.

The first pixels PX1, the second pixels PX2, and the sensor units SU may have different sensing resolutions from one another. The number of second pixels PX2 and the number of sensor units SU may be determined based on the sensing resolutions relative to, for example, to the number of first pixels PX1. In one embodiment, the second pixels PX2 and the sensor units SU may have lower resolutions than the first pixels PX1.

A light shielding member 170 may be arranged between the sensor units SU and the substrate 101. The light shielding member 170 may shield against light of the first wavelength band, which may fall incident to the sensor units SU from an external environment.

The scan driver 200 outputs scan signals via the plurality of scan lines SL. In one embodiment, the scan driver 200 may sequentially drive the scan lines SL.

The data driver 300 outputs data signals via the plurality of data lines DL.

The sensing signal processor 400 may receive sensing signals from the plurality of read out lines RL and process the received sensing signals. The sensing signal processor 400 may include an integrator (e.g., 420 of FIG. 3) connected to the read out lines RL.

The controller 500 may generate control signals for controlling the scan driver 200, the data driver 300, and the sensing signal processor 400. The controller 500 may generate biometric information from signals output from the sensing signal processor 400, and may generate image data corresponding to the biometric information and output the generated image data via the data driver 300.

The scan driver 200, the data driver 300, the sensing signal processor 400, and the controller 500 may be formed as separate integrated circuit (IC) chips or an integral IC chip, and may be directly mounted in a non-display area around the display area of the substrate 101, mounted on a flexible printed circuit film, coupled to the substrate 101 as a tape carrier package (TCP), or directly formed on the substrate 101.

In the present embodiment, display unit A includes only the first pixels PX1 that emit visible rays of light. In another embodiment, the display unit A may include third pixels PX3 that are arranged in the same layer as the first pixels PX1 and that emit white light. In this case, color filters corresponding to optical paths of light emitted from the first pixels PX1 and the third pixels PX3, respectively, may be included.

Figure 3:
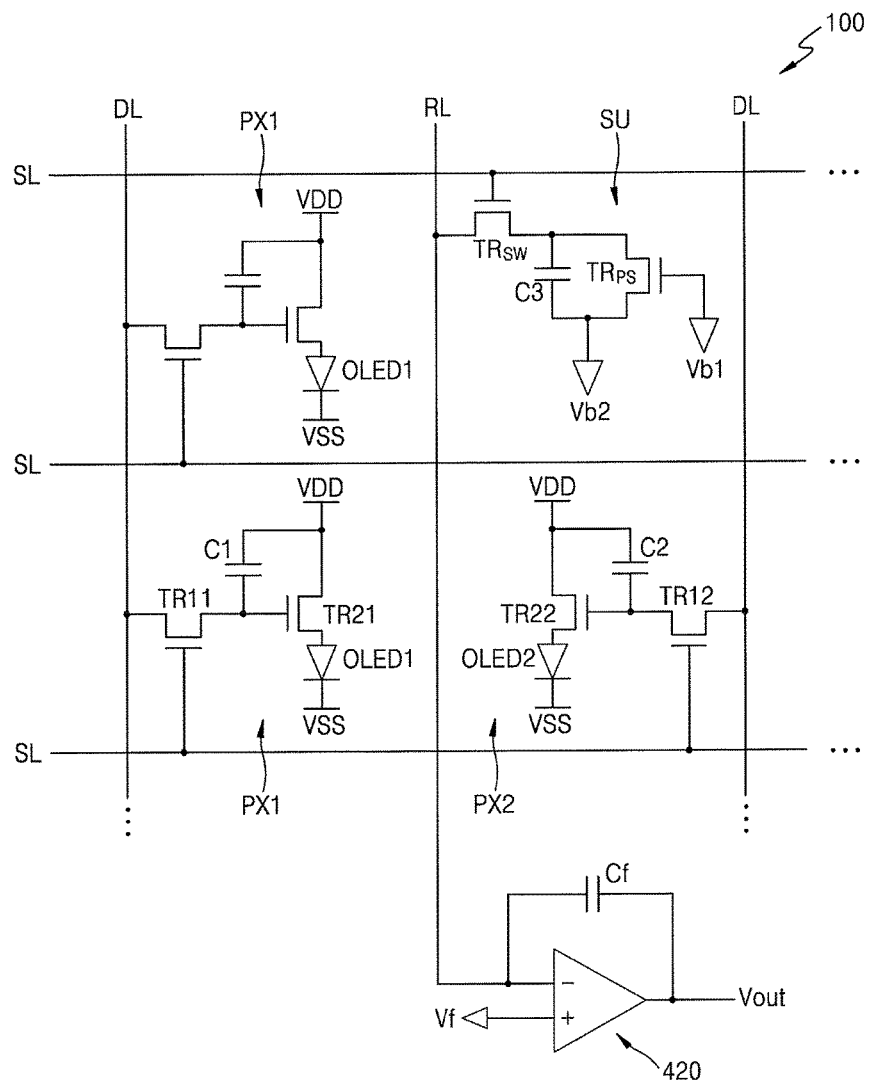
FIG. 3 illustrates a circuit embodiment of the display panel.

FIG. 3 illustrates a circuit embodiment of the display panel 100, which in this partial diagram includes a representative sampling of a sensor unit SU, first pixels PX1, and a second pixel PX2.

Referring to FIG. 3, each of the first pixels PX1 includes a first pixel circuit, which includes a first transistor TR11, a second transistor TR21, and a first capacitor C1. A first light-emitting device OLED1 is connected to the first pixel circuit. The first transistor TR11 may include a gate electrode connected to a corresponding scan line SL, a first electrode connected to a corresponding data line DL, and a second electrode. The first and second electrodes may be source and drain electrodes.

The second transistor TR21 may include a gate electrode connected to the second electrode of the first transistor TR11, a first electrode connected to a power line for applying a first power voltage VDD, and a second electrode connected to the first organic light-emitting device OLED1. The first and second electrodes may be source and drain electrodes.

The first capacitor C1 may include a first electrode and a second electrode. The first electrode of the first capacitor C1 may be connected to the second electrode of the first transistor TR11 and the gate electrode of the second transistor TR21. The second electrode of the first capacitor C1 may be connected to the power line for applying the first power voltage VDD.

The first light-emitting device OLED1 may be an organic light-emitting diode, including a first electrode connected to the second electrode of the second transistor TR21, a second electrode facing the first electrode, and a first emission layer between the first electrode and the second electrode. The first emission layer may emit light, for example, in a visible light range of about 380 to about 750 nm.

The first transistor TR11 of the first pixels PX1 is turned-on in response to a scan signal from the corresponding scan line. The first transistor transmits a data signal from the corresponding data line to the first capacitor C1, and the first capacitor C1 is charged with a voltage corresponding to the data signal. A driving current corresponding to the voltage charged in the first capacitor C1 is transmitted to the first light-emitting device OLED1 via the second transistor TR21, so that the first light-emitting device OLED1 emits light.

The second pixels PX2 include a second pixel circuit including a third transistor TR12, a fourth transistor TR22, and a second capacitor C2. A second light-emitting device OLED2 is connected to the second pixel circuit. The third transistor TR12 may include a gate electrode connected to a corresponding scan line SL, a first electrode connected to a corresponding data line DL, and a second electrode. The first and second electrodes may be source and drain electrodes.

The fourth transistor TR22 may include a gate electrode connected to the second electrode of the third transistor TR12, a first electrode connected to the power line applying the first power voltage VDD, and a second electrode connected to the second light-emitting device OLED2. The first and second electrodes electrode may be source and drain electrodes.

The second capacitor C2 may include a first electrode and a second electrode. The first electrode of the second capacitor may be connected to the second electrode of the third transistor TR12 and the gate electrode of the fourth transistor TR22. The second electrode of the second capacitor C2 may be connected to the power line for applying the first power voltage VDD.

The second light-emitting device OLED2 may be an organic light-emitting diode, including a first electrode connected to the second electrode of the fourth transistor TR22, a second electrode facing the first electrode, and a second emission layer between the first electrode and the second electrode. The second emission layer may emit light, for example, in the IR range of about 750 to about 1000 nm.

The third transistor TR12 of the second pixels PX2 is turned-on in response to a scan signal from the corresponding scan line. The third transistor TR12 transmits a data signal from the corresponding data line to the second capacitor C2 and the second capacitor C2 is charged with a voltage corresponding to the data signal. A driving current corresponding to the voltage charged in the second capacitor C2 is transmitted to the second light-emitting device OLED2 via the fourth transistor TR22, so that the second light-emitting device OLED2 emits light.

The sensor unit SU may include a switching transistor TRsw, a sensing transistor TRps, and a third capacitor C3. The switching transistor TRsw may include a gate electrode connected to a corresponding scan line SL, a first electrode connected to a corresponding read out line RL, and a second electrode.

The sensing transistor TRps is a light sensing device and senses IR light. The sensing transistor TRps may include a gate electrode connected to a first bias line applying a first bias voltage Vb1, a first electrode connected to the second electrode of the switching transistor TRsw, and a second electrode connected to a second bias line applying a second bias voltage Vb2. The first bias voltage Vb1 may be a sufficiently low or high voltage, so that the sensing transistor TRps may maintain a turn-off state when IR light is not irradiated to the sensing transistor TRps.

The third capacitor C3 may include a first electrode and a second electrode. The first electrode of the third capacitor C3 is connected to the first electrode of the sensing transistor TRps and the second electrode of the switching transistor TRsw. The second electrode of the third capacitor C3 is connected to the second bias line.

The switching transistor TRsw is turned on in response to a scan signal from the corresponding scan line SL, and the third capacitor C3 is charged in correspondence to a difference between a voltage from the corresponding read out line RL and the second bias voltage Vb2 from the second bias line. When the switching transistor TRsw is turned off, and IR light is incident on the sensing transistor TRps from the outside, the sensing transistor TRps generates a light (leakage) current corresponding to the amount of light. Due to the light current, the charged voltage of the third capacitor C3 is changed. When the switching transistor TRsw is turned on as a scan signal is supplied again from the scan line SL, a sensing signal corresponding to the changed charged voltage of the third capacitor C3 is output, via the read out line RL, via the switching transistor TRsw. The sensing signal output via the read out line RL is input into the integrator 420.

The integrator 420 may include an amplifier AP having an inverting terminal (−), non-inverting terminal (+), and an output terminal, and a capacitor Cf. The inverting terminal (−) is connected to a read out line RL. The capacitor Cf is connected between the inverting terminal (−) and the output terminal. The non-inverting terminal (+) is connected to a supply source of a reference voltage Vf. The amplifier AP and the capacitor Cf may integrate the sensing signal from the read out line RL for a certain time and generate an output signal Vout.

In the present embodiment, each of the first pixels PX1 and the second pixels PX2 have two transistors and one capacitor. One or both of the first or second pixels PX1 and PX2 may have a different number and/or structure of elements in another embodiment, e.g., one of the pixels may have more than two transistors and/or more than one capacitor.

Figure 4:
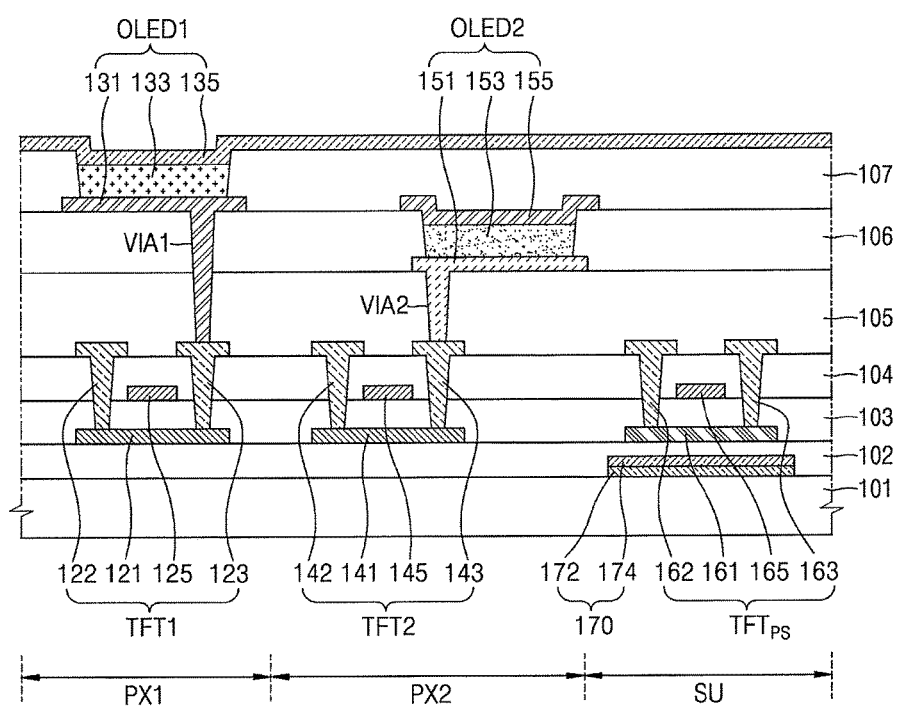
FIG. 4 illustrates a partial cross-sectional view of the display panel.

FIG. 4 is a partial cross-sectional view of the display panel 100. Referring to FIG. 4, the first pixel PX1, the second pixel PX2, and the sensor unit SU may be arranged in the display area of the substrate 101. The first pixel PX1 includes the first pixel circuit and the first light-emitting device OLED1 connected to the first pixel circuit. FIG. 4 illustrates a thin film transistor corresponding to the second transistor TR21 of the first pixel circuit. This structure may likewise be applied to the first transistor TR11. Thus, hereinafter, the transistor will be commonly described as a first thin film transistor TFT1, for convenience of explanation.

The first thin film transistor TFT1 includes a first semiconductor layer 121, a first source electrode 122, a first drain electrode 123, and a first gate electrode 125. The first semiconductor layer 121 may include polysilicon (poly-Si). A first insulating layer 103 may be between the first semiconductor layer 121 and the first gate electrode 125, as a gate insulating layer. A second insulating layer 104 may be between the first source electrode 122 and the first drain electrode 123, and the first gate electrode 125, as an interlayer insulating layer. The first source electrode 122 and the first drain electrode 123 may be electrically connected to the first semiconductor layer 121 via contact holes in the first insulating layer 103 and the second insulating layer 104, respectively. The first pixel circuit including the first thin film transistor TFT1 may at least partially overlap the first light-emitting device OLED1 in a vertical direction or may not overlap the first light-emitting device OLED1.

The first light-emitting device OLED1 includes a first electrode 131, a second electrode 135, and a first intermediate layer 133 between the first electrode 131 and the second electrode 135. The first intermediate layer 133 may include a first emission layer that emits light in, for example, a visible wavelength band in a direction opposite to (away from) the substrate 101. The first light-emitting device OLED1 may be electrically connected to the first thin film transistor TFT1 via a first via hole VIA1 in a third insulating layer 105 and a fourth insulating layer 106. The first electrode 131 may be a reflection electrode and the second electrode 135 may be a transparent electrode.

The second pixel PX2 includes the second pixel circuit and the second light-emitting device OLED2 connected to the second pixel circuit. FIG. 4 illustrates a thin film transistor corresponding to the fourth transistor TR22 of the second pixel circuit. This structure may likewise be applied to the third transistor TR12. Thus, hereinafter, the transistor will be described commonly as a second thin film transistor TFT2, for convenience of explanation.

The second thin film transistor TFT2 includes a second semiconductor layer 141, a second source electrode 142, a second drain electrode 143, and a second gate electrode 145. The second semiconductor layer 141 may include poly-Si. The first insulating layer 103 may be between the second semiconductor layer 141 and the second gate electrode 145, as a gate insulating layer. The second insulating layer 104 may be between the second source electrode 142 and the second drain electrode 143, and the second gate electrode 145, as an interlayer insulating layer. The second source electrode 142 and the second drain electrode 143 may be electrically connected to the second semiconductor layer 141 via contact holes in the first insulating layer 103 and the second insulating layer 104, respectively. The second pixel circuit including the second thin film transistor TFT2 may not overlap the second light-emitting device OLED2.

The second light-emitting device OLED2 includes a first electrode 151, a second electrode 155, and a second intermediate layer 153 between the first electrode 151 and the second electrode 155. The second intermediate layer 153 may include a second emission layer that emits light, for example, in an IR wavelength band in a direction toward the substrate 101. The second light-emitting device OLED2 may be electrically connected to the second thin film transistor TFT2 via a second via hole VIA2 in the third insulating layer 105. The first electrode 151 may be a transparent electrode and the second electrode 155 may be a reflection electrode.

The second light-emitting device OLED2 may be arranged below (or at a layer below) the first light-emitting device OLED1. For example, at least the second emission layer 153 of the second light-emitting device OLED2 may be below the first emission layer 133 of the first light-emitting device OLED1.

The second light-emitting device OLED2, below the first light-emitting device OLED1, may be spaced apart from the first light-emitting device OLED1 by a certain distance in a horizontal direction, as seen from a cross-sectional point of view. Thus, the second light-emitting device OLED2 may not overlap the first light-emitting device OLED1. As a result, signal interference and/or color interference between the first light-emitting device OLED1 and the second light-emitting device OLED2 may be reduced or minimized.

The sensor unit SU may include the switching transistor TRsw and the sensing transistor TRps. In FIG. 4, a thin film transistor corresponding to the sensing transistor TRps is illustrated and thus may be referred to as the sensing thin film transistor TFTps. The switching transistor TRsw may have the same structure as the first thin film transistor TFT1 of the first pixel PX1 or the second thin film transistor TFT2 of the second pixel PX2.

The sensing thin film transistor TFTps includes a third semiconductor layer 161, a third source electrode 162, a third drain electrode 163, and a third gate electrode 165.

The third semiconductor layer 161 is a light-receiving layer which may include a semiconductor material sensitive to IR light. For example, the third semiconductor layer 161 may include amorphous silicon germanium (a-SiGe). Sensitivity for IR light of the third semiconductor layer 161 may be adjusted based on a composition ratio of $SiH_4$ and $GeH_4$ in the third semiconductor layer 161.

Figure 5A:
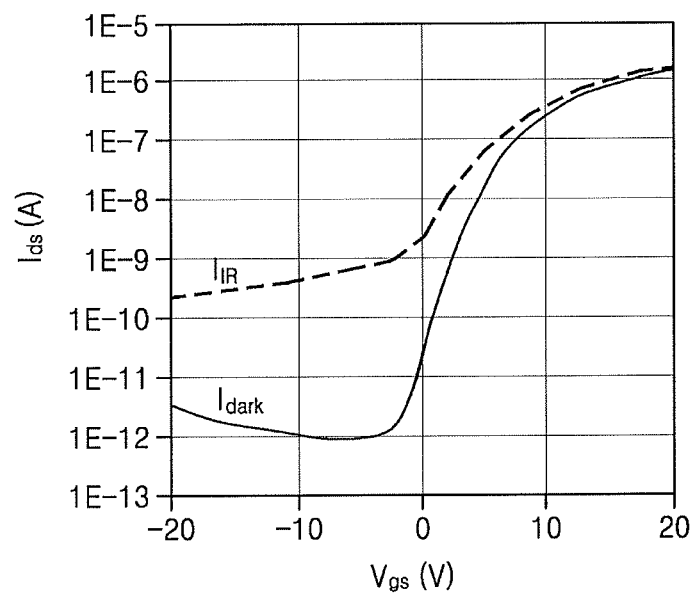
FIGS. 5A to 5C illustrate examples of relationships between a gate-source voltage and a light current of a sensing thin film transistor.
Figure 5B:
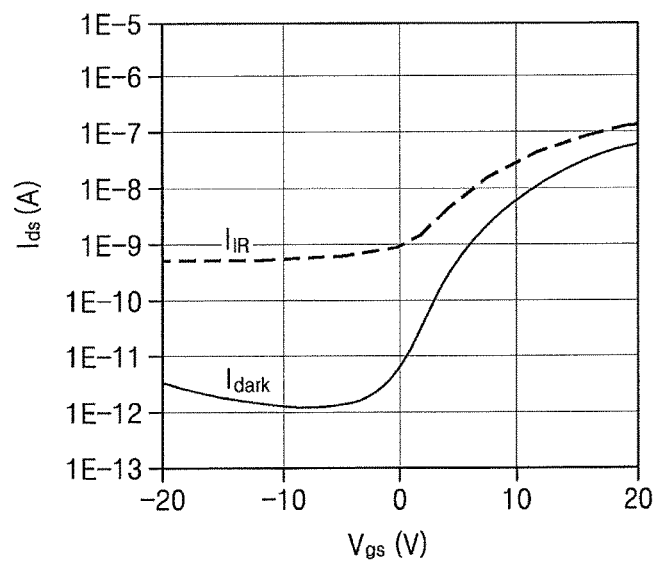
Figure 5C:
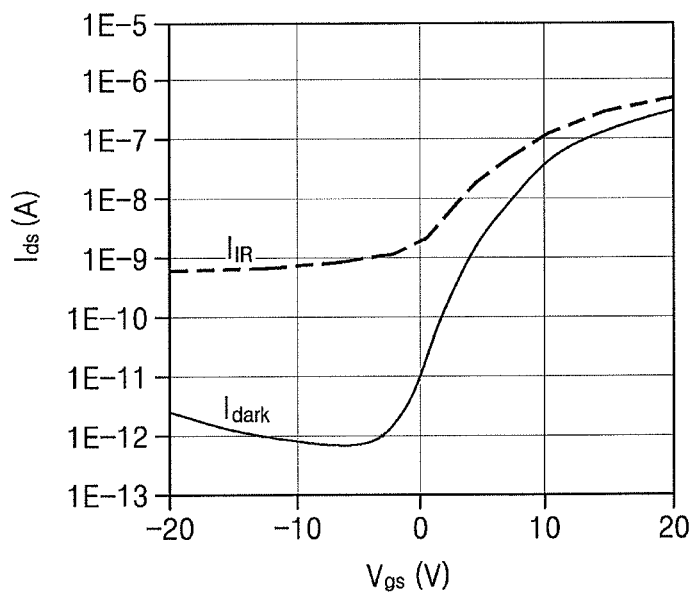

FIGS. 5A to 5C are graphs illustrating examples of a relationship between a gate-source voltage Vgs and a light current Ids of the sensing thin film transistor TFTps based on the composition of the third semiconductor layer 161. In FIGS. 5A through 5C, I_IR is a light current based on the gate-source voltage Vgs in a state in which the third semiconductor layer 161 is exposed to IR light. I_dark is a light current based on the gate-source voltage Vgs in a state in which the third semiconductor layer 161 is blocked from external light.

Referring to FIGS. 5A to 5C, the magnitude of the light current Ids and an IR sensitivity of the sensing thin film transistor TFTps may vary in a turn-off area based on the composition ratio of $SiH_4$ and $GeH_4$ in the third semiconductor layer 161 including a-SiGe. The IR sensitivity may be calculated by a ratio of an I_IR graph to an I_dark graph. When the composition ratio ($SiH_4$:$GeH_4$) of $SiH_4$ to $GeH_4$ in FIG. 5C is 1:2, the IR sensitivity may be considered to be relatively high.

In one embodiment, the third semiconductor layer 161 may include any material which is sensitive to IR light. The first insulating layer 103 may be between the third semiconductor layer 161 and the third gate electrode 165 as a gate insulating layer. The second insulating layer 104 may be between the third source electrode 162 and the third drain electrode 163, and the third gate electrode 165, as an interlayer insulating layer. The third source electrode 162 and the third drain electrode 163 may be electrically connected to the third semiconductor layer 161 via contact holes in the first insulating layer 103 and the second insulating layer 104, respectively.

The light shielding member 170 may be below the third semiconductor layer 161. An insulating layer may be between the third semiconductor layer 161 and the light shielding member 170, and the insulating layer may be a portion of the buffer layer 102.

The light shielding member 170 is a layer for preventing visible rays from being incident on the third semiconductor layer 161. The light shielding member 170 may include at least one of an organic material including a black pigment, amorphous silicon, a-SiGe, or a-Ge. In the embodiment of FIG. 4, an example of a stack of a first light shielding layer 172 including a-Ge and a second light shielding layer 174 including a-SiGe, which is above the first light shielding layer 172, is illustrated.

Figure 6:
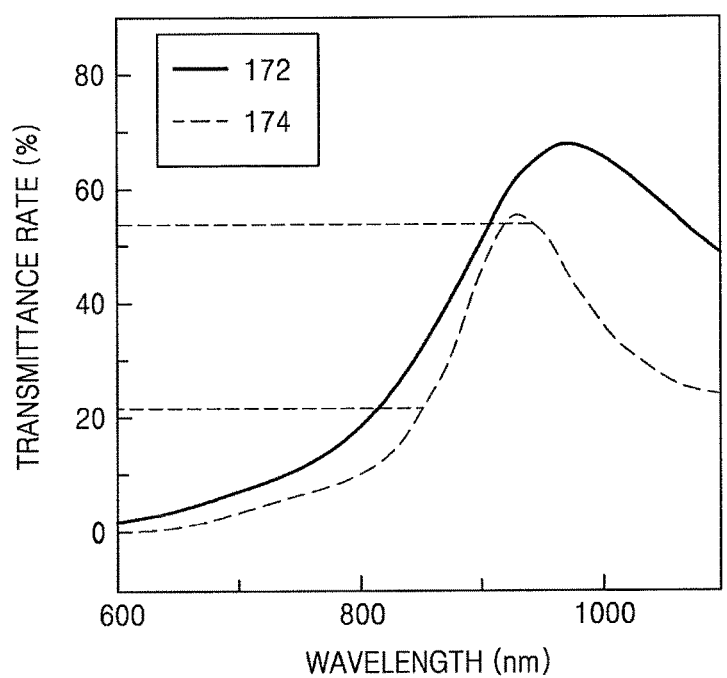
FIG. 6 illustrates an example of the transmittance rate of a light shielding member based on wavelength.

FIG. 6 is a graph illustrating an example of a transmittance rate of the light shielding member 170 according to a wavelength of the light shielding member 170. Referring to FIG. 6, the first light shielding layer 172 including a-Ge and the second light shielding layer 174 including a-SiGe may have a low transmittance rate of the visible light range of a wavelength band, for example, of about 400 to about 750 nm, and may have a high transmittance rate of the IR range of a wavelength band, for example, of about 750 to about 1000 nm. Thus, due to a double layer structure including the first light shielding layer 172 including a-Ge and the second light shielding layer 174 including a-SiGe, the transmittance rate of visible rays may be decreased and the transmittance rate of the IR rays may be increased.

In one embodiment, the light shielding member 170 may include any material, through which light of the IR range easily penetrates and light of the visible light range does not easily penetrate. In one embodiment, the light shielding member 170 may be greater than the third semiconductor layer 161 in order to cover the entire third semiconductor layer 161.

Figure 7A:
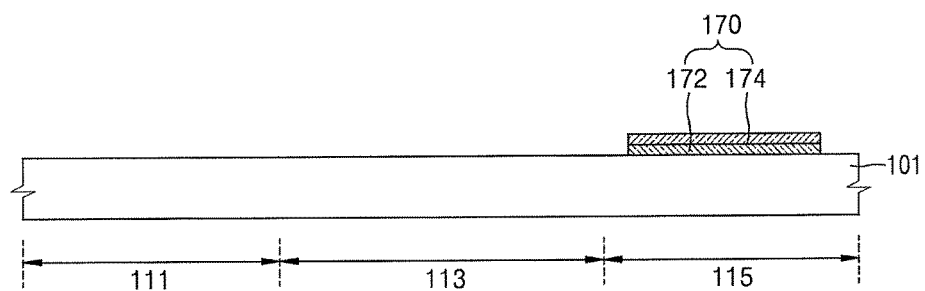
FIGS. 7A to 7J illustrate an embodiment of a method for manufacturing a display panel.

FIGS. 7A to 7J illustrate an embodiment of a method for manufacturing a display panel, for example, as illustrated in FIG. 4. Referring to FIG. 7A, the light shielding member 170 may be formed on the substrate 101. The substrate 101 may include various materials, e.g., glass, metal, plastic, etc. According to an embodiment, the substrate 101 may include a substrate including a flexible material. The substrate 101 may include a first area 111 including the first pixels PX1, a second area 113 including the second pixels PX2, and a third area 115 including the sensor units SU.

After a first light shielding material layer and a second light shielding material layer are stacked on the third area 115 of the substrate 101, the first light shielding material layer and the second light shielding material layer may be patterned by a photomask process to form the light shielding member 170, including the first light shielding layer 172 and the second light shielding layer 174. The first light shielding layer 172 may include a-Ge and the second light shielding layer 174 may include a-SiGe.

Figure 7B:
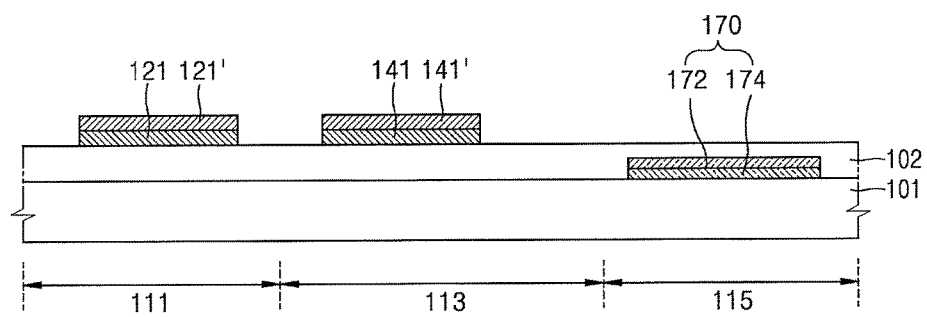

Referring to FIG. 7B, the first semiconductor layer 121 and the second semiconductor layer 141 may be formed on the substrate 101 on which the light shielding member 170 is formed. The buffer layer 102 may be formed throughout the substrate 101 to cover the light shielding member 170. The buffer layer 102 may be formed as a single layer or multiple layers including, for example, an inorganic material, e.g., $SiN_x$ and/or $SiO_x$.

The first semiconductor layer 121 may be formed in the first area 111 and the second semiconductor layer 141 may be formed in the second area 113. These layers may be formed, for example, by forming semiconductor layers on the buffer layer 102 using a semiconductor material and patterning the semiconductor layers by a photomask process. The first semiconductor layer 121 and the second semiconductor layer 141 may include the same material. In one embodiment, the first semiconductor layer 121 and the second semiconductor layer 141 may include an inorganic semiconductor material, e.g., a-Si or poly-Si. Poly-Si may be formed by crystallizing a-Si. Various methods of crystallizing a-Si may be used. Examples include as rapid thermal annealing (RTA), solid phase crystallization (SPC), excimer laser annealing (ELA), metal induced crystallization (MIC), metal induced lateral crystallization (MILC), sequential lateral solidification (SLS), etc.

After a dry etching process is performed for patterning the first semiconductor layer 121 and the second semiconductor layer 141, a strip process may be omitted. Thus, photosensitive layers 121' and 141' may remain on patterns of the first semiconductor layer 121 and the second semiconductor layer 141. The photosensitive layers 121' and 141' may protect the first semiconductor layer 121 and the second semiconductor layer 141 from a dry etching process for forming the third semiconductor layer 161.

Figure 7C:
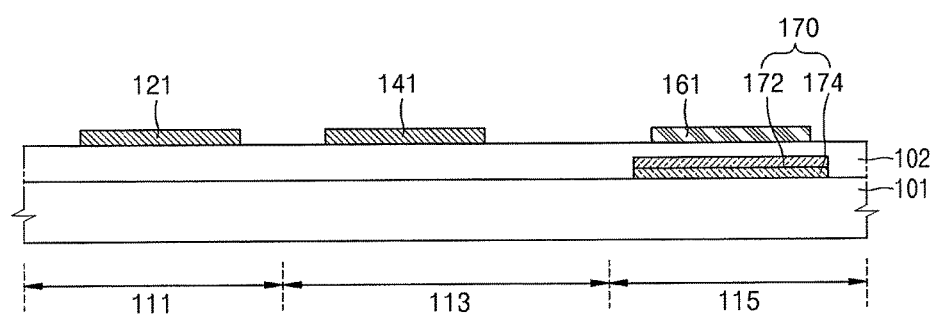

Referring to FIG. 7C, the third semiconductor layer 161 may be formed in the third area 115, for example, by forming a semiconductor layer on the buffer layer 102 using a semiconductor material and patterning the semiconductor layer by a photomask process. The third semiconductor layer 161 may include a-SiGe. The third semiconductor layer 161 may vertically overlap the light shielding member 170 as seen from a cross-sectional point of view.

After the dry etching process for patterning the third semiconductor layer 161, the photosensitive layers 121' and 141' on the first and second semiconductor layers 121 and 141 and a photosensitive layer on the third semiconductor layer 161 may be removed by a strip process.

Figure 7D:
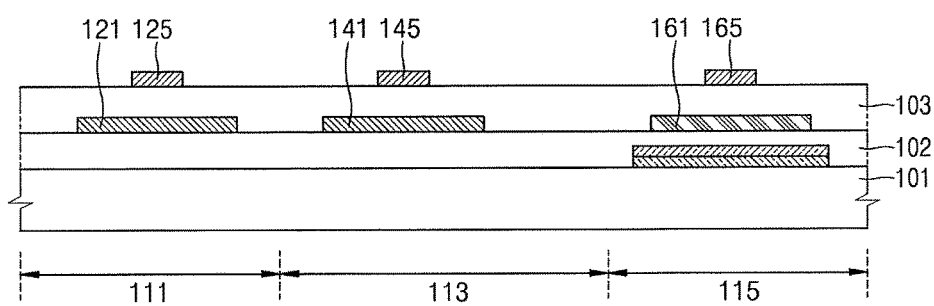

Referring to FIG. 7D, the first through third gate electrodes 125, 145, and 165 may be formed on the substrate 101 on which the first through third semiconductor layers 121, 141, and 161 are formed. The first insulating layer 103 may be formed throughout the substrate 101 to cover the first through third semiconductor layers 121, 141, and 161. The first insulating layer 103 may be formed as a single layer or multiple layers including an inorganic material, e.g., $SiO_2$, $SiN_x$, SiON, $Al_2O_3$, $TiO_2$, $Ta_2O_5$, $HfO_2$, and/or $ZrO_2$.

The first gate electrode 125 of the first area 111, the second gate electrode 145 of the second area 113, and the third gate electrode 165 of the third area 115 may be formed by forming a conductive layer on the first insulating layer 103 and patterning the conductive layer. The first through third gate electrodes 125, 145, and 165 may be connected to scan lines. Each of the first through third gate electrodes 125, 145, and 165 may include a single layer or multiple layers including at least one of Al, Pt, Pd, Ag, Mg, Au, Ni, Nd, Ir, Cr, Li, Ca, Mo, Ti, W, or Cu. The first through third gate electrodes 125, 145, and 165 may vertically overlap at least portions of the first through third semiconductor layers 121, 141, and 161, respectively, as seen from a cross-sectional point of view.

Figure 7E:
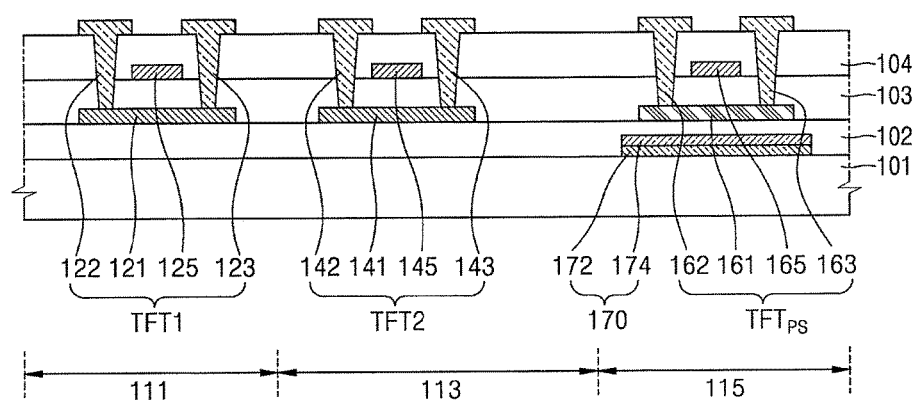

Referring to FIG. 7E, the first through third source electrodes 122, 142, and 162, and the first through third drain electrodes 123, 143, and 163 may be formed on the substrate 101 on which the first through third gate electrodes 125, 145, and 165 are formed. The second insulating layer 104 may be formed throughout the substrate 101 to cover the first through third gate electrodes 125, 145, and 165. The second insulating layer 104 may be formed as a single layer or multiple layers including an organic material (e.g., polyimide, polyester, acryl, etc.) or may be formed as a single layer or multiple layers including an inorganic material like the first insulating layer 103. Alternatively, the second insulating layer 104 may be formed by alternating an organic material and an inorganic material.

Next, contact holes exposing portions of the first through third semiconductor layers 121, 141, and 161 may be formed in the first insulating layer 103 and the second insulating layer 104.

Thereafter, a conductive layer may be formed on the second insulating layer 104. The conductive layer may be patterned to form the first source electrode 122 and the first drain electrode 123 of the first area 111, the second source electrode 142, and the second drain electrode 143 of the second area 113, and the third source electrode 162 and the third drain electrode 163 of the third area 115. The first through third source electrodes 122, 142, and 162 and the first through third drain electrodes 123, 143, and 163 may include substantially the same material as the first through third gate electrodes 125, 145, and 165. The first through third source electrodes 122, 142, and 162 and the first through third drain electrodes 123, 143, and 163 may be electrically connected to the first through third semiconductor layers 121, 141, and 161 therebelow, respectively, via the contact holes.

Figure 7F:
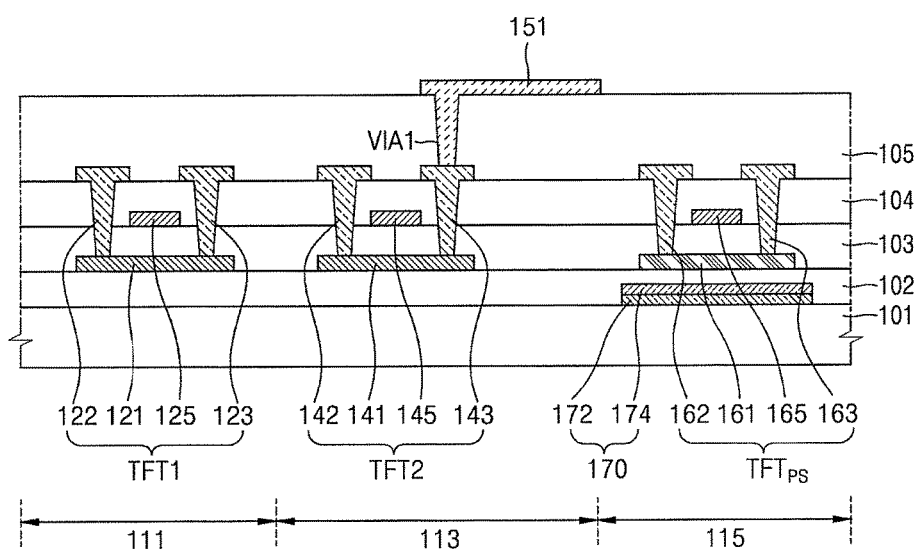

Referring to FIG. 7F, the first electrode 151 of the second light-emitting device OLED2 may be formed on the substrate 101 on which the thin film transistors are formed. The third insulating layer 105 may be formed throughout the substrate 101 to cover the thin film transistors. The third insulating layer 105 may be formed as a single layer or multiple layers including an organic material or an inorganic material, like the second insulating layer 104. Alternatively, the third insulating layer 105 may be formed by alternating an organic material and an inorganic material.

Next, the first via hole VIA1 exposing a portion of the second source electrode 142 or the second drain electrode 143 (the second drain electrode, in the case of FIG. 7F) of the second area 113 may be formed in the third insulating layer 105.

Then, a conductive layer may be formed on the third insulating layer 105 of the second area 113 and may be patterned to form the first electrode 151 of the second light-emitting device OLED2 in the second area 113. The first electrode 151 of the second light-emitting device OLED2 may be electrically connected to the second drain electrode 143 via the first via hole VIA1. The first electrode 151 of the second light-emitting device OLED2 may include a transparent conductive material. The transparent conductive material may include, for example, at least one selected from indium tin oxide (ITO), indium zinc oxide (IZO), zinc oxide (ZnO), indium oxide ($In_2O_3$), indium gallium oxide (IGO), or aluminum zinc oxide (AZO).

Figure 7G:
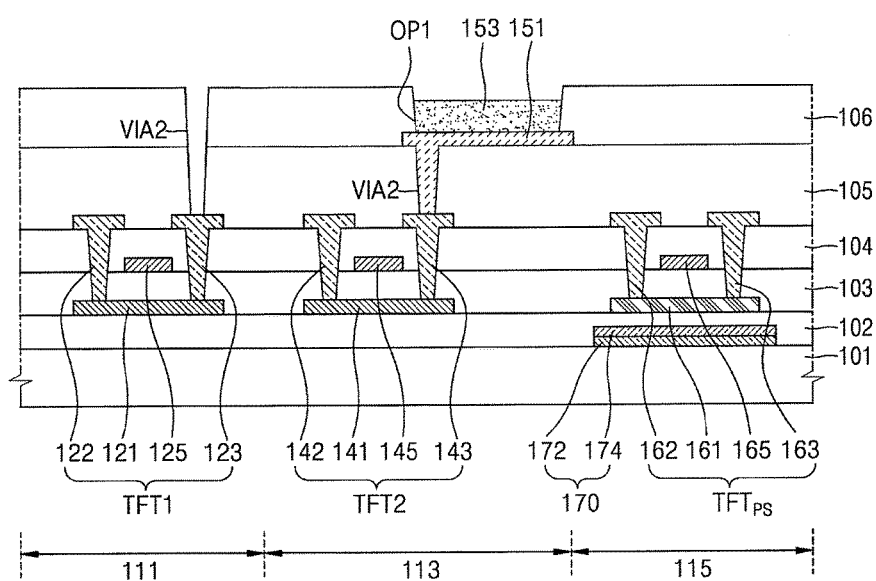

Referring to FIG. 7G, the fourth insulating layer 106 may be formed on the substrate 101 on which the first electrode 151 of the second light-emitting device OLED2 is formed. The fourth insulating layer 106 may be formed as a single layer or multiple layers including an organic material or an inorganic material, like the second insulating layer 104. Alternatively, the fourth insulating layer 106 may be formed by alternating an organic material and an inorganic material.

Next, a first opening OP1 exposing a portion of the first electrode 151 of the second light-emitting device OLED2 and the second via hole VIA2 exposing a portion of the first source electrode 122 or the first drain electrode 123 (the first drain electrode, in the case of FIG. 7G) of the first area 111 may be formed in the fourth insulating layer 106. The fourth insulating layer 106 may cover an edge of the first electrode 151 of the second light-emitting device OLED2.

Thereafter, the second intermediate layer 153 including the second emission layer may be formed on the first electrode 151 in the first opening OP1 of the second area 113. The second emission layer may emit light of the IR range.

Figure 7H:
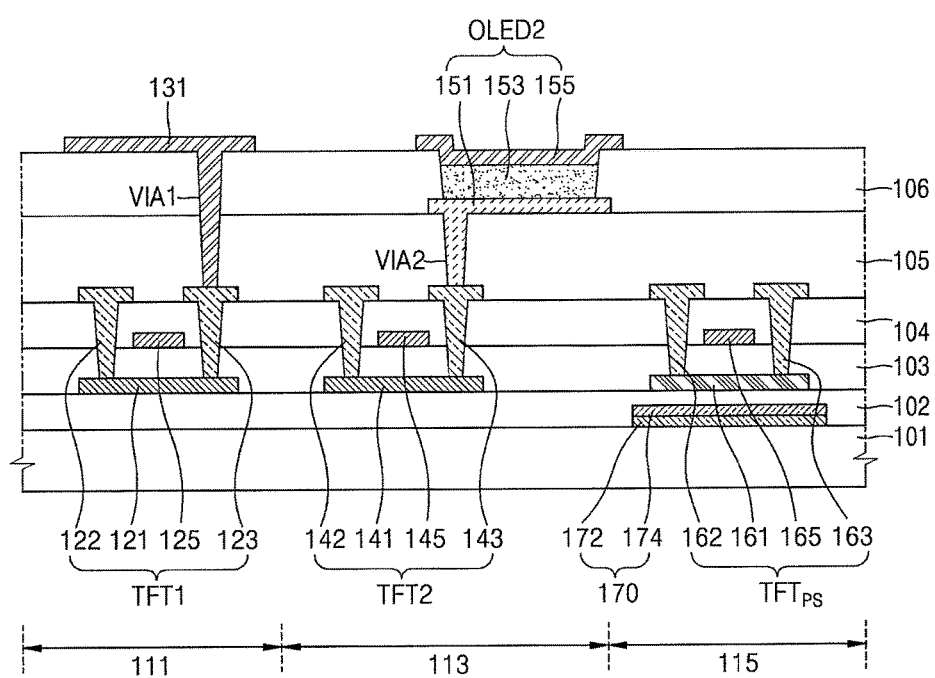

Referring to FIG. 7H, the first electrode 131 of the first light-emitting device OLED1 and the second electrode 155 of the second light-emitting device OLED2 may be formed on the substrate 101 on which the fourth insulating layer 106 and the second intermediate layer 153 are formed.

A conductive layer may be formed throughout the substrate 101 and may be patterned to form the first electrode 131 in the first area 111 and the second electrode 155 in the second area 113. The first electrode 131 of the first light-emitting device OLED1 may be electrically connected to the first drain electrode 123 via the second via hole VIA2. The first electrode 131 of the first light-emitting device OLED1 and the second electrode 155 of the second light-emitting device OLED2 may include the same reflective conductive material. The reflective conductive material may include, for example, at least one metal selected from the group of Ag, Mg, Al, Pt, Pd, Au, Ni, Nd, Ir, Cr, Li, Ca, and an alloy thereof.

In the embodiment of FIG. 7H, it is described that the first electrode 131 of the first light-emitting device OLED1 and the second electrode 155 of the second light-emitting device OLED2 include the same material. In one embodiment, the first electrode 131 of the first light-emitting device OLED1 and the second electrode 155 of the second light-emitting device OLED2 may be manufactured by separate processes using different materials.

Figure 7I:
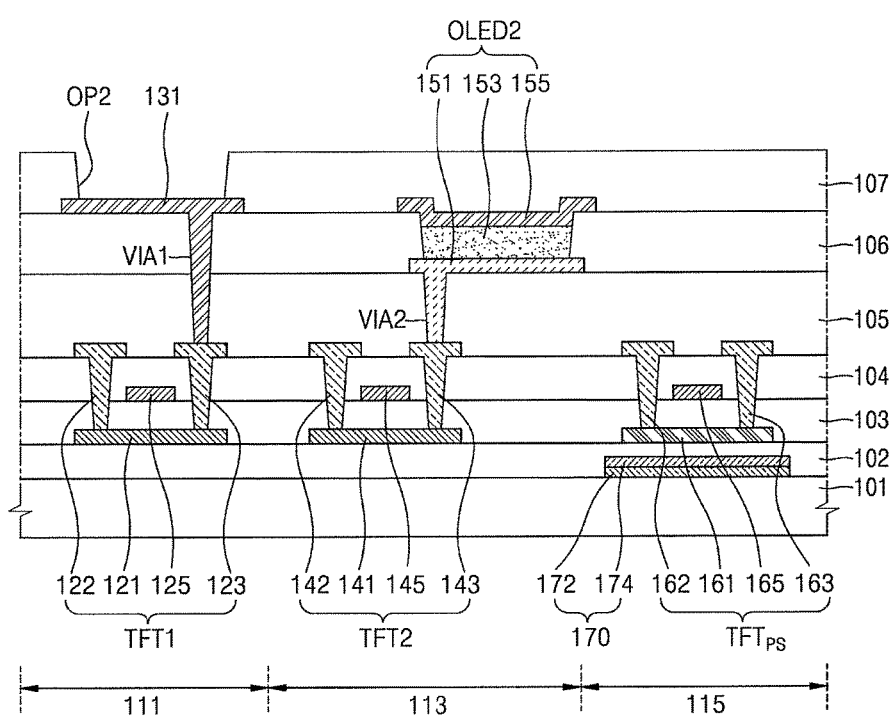

Referring to FIG. 7I, a fifth insulating layer 107 may be formed on the substrate 101 on which the first electrode 131 of the first light-emitting device OLED1 and the second light-emitting device OLED2 are formed. The fifth insulating layer 107 may be formed as a single layer or multiple layers including an organic material or an inorganic material, like the second insulating layer 104. Alternatively, the fifth insulating layer 107 may be formed by alternating an organic material and an inorganic material.

Next, a second opening OP2 exposing a portion of the first electrode 131 of the first light-emitting device OLED1 may be formed in the fifth insulating layer 107. The fifth insulating layer 107 may cover an edge of the first electrode 131 of the first light-emitting device OLED1.

Figure 7J:
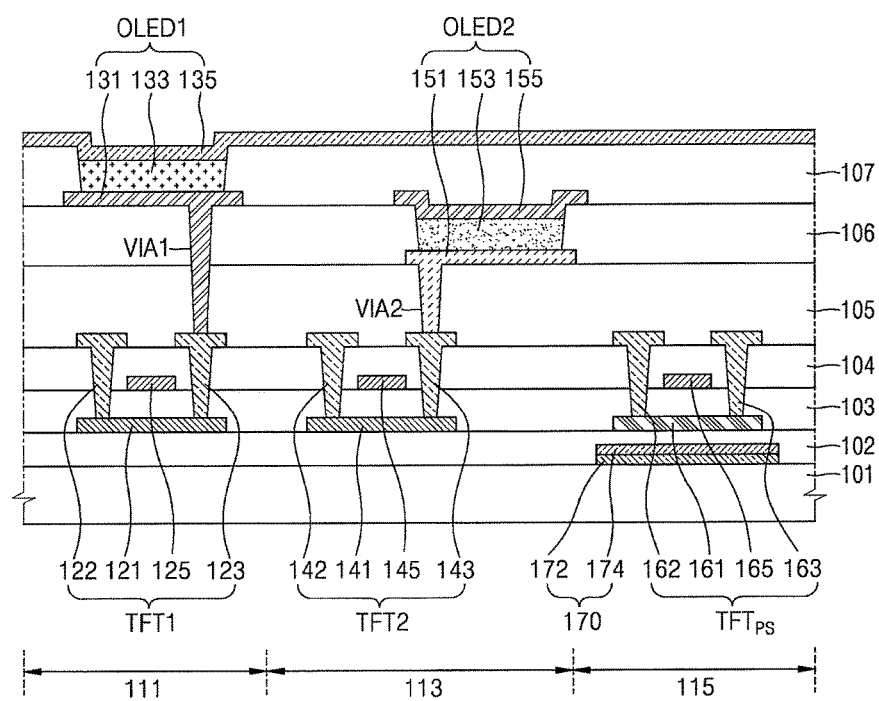

Referring to FIG. 7J, the first intermediate layer 133 including the first emission layer and the second electrode 135 may be formed on the first electrode 131 in the second opening OP2 of the first area 111. The second electrode 135 of the first light-emitting device OLED1 may be formed throughout the substrate 101. The first emission layer may emit light of a visible ray range.

Figure 8:
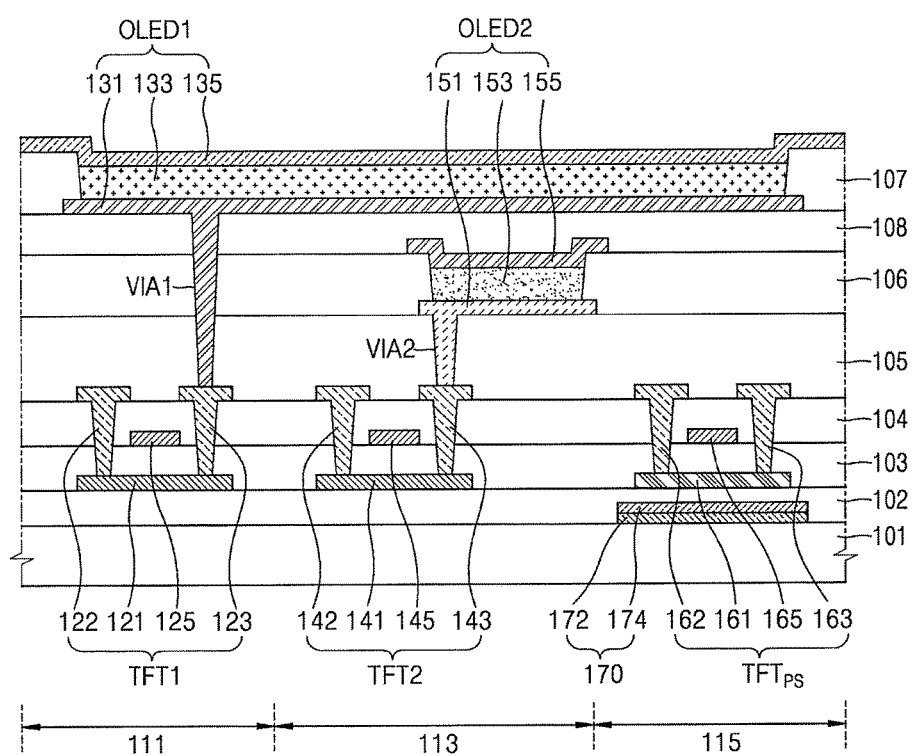
FIG. 8 illustrates another embodiment of a display panel.

FIG. 8 illustrates another embodiment of a display panel. This embodiment differs from the embodiment in FIG. 4 in that a sixth insulating layer 108 is further included between the first light-emitting device OLED1 of the first pixel PX1 and the second light-emitting device OLED2 of the second pixel PX2.

The second light-emitting device OLED2 of the second pixel PX2 may be arranged below (or at a layer below) the first light-emitting device OLED1 of the first pixel PX1. For example, at least the second emission layer 153 of the second light-emitting device OLED2 may be below the first emission layer 133 of the first light-emitting device OLED1.

The first light-emitting device OLED1 of the first pixel PX1 and the second light-emitting device OLED2 of the second pixel PX2 may at least partially overlap each other in a vertical direction, as seen from a cross-sectional point of view. The second light-emitting device OLED2 below the first light-emitting device OLED1 may at least partially overlap the first light-emitting device OLED1 in the vertical direction. When the first light-emitting device OLED1 of the first pixel PX1 and the second light-emitting device OLED2 of the second pixel PX2 at least partially overlap each other, aperture ratios of the first pixel PX1 and the second pixel PX2 may increase. In one embodiment, the first pixel PX1 may be greater than the second pixel PX2.

In order to reduce or minimize signal interference and/or color interference between the first light-emitting device OLED1 and the second light-emitting device OLED2, the sixth insulating layer 108 may further be included between the first light-emitting device OLED1 and the second light-emitting device OLED2. The sixth insulating layer 108 may be formed as a single layer or multiple layers including an organic material or an inorganic material, like the second insulating layer 104. Alternatively, the sixth insulating layer 108 may be formed by alternating an organic material and an inorganic material.

In one embodiment, the second light-emitting device OLED2 below the sixth insulating layer 108 may be spaced apart from a side surface of the first light-emitting device OLED1. Because the second light-emitting device OLED2 is below the first light-emitting device OLED1, the second light-emitting device OLED2 does not overlap the first light-emitting device OLED1 as seen from a cross-sectional point of view.

Figure 9:
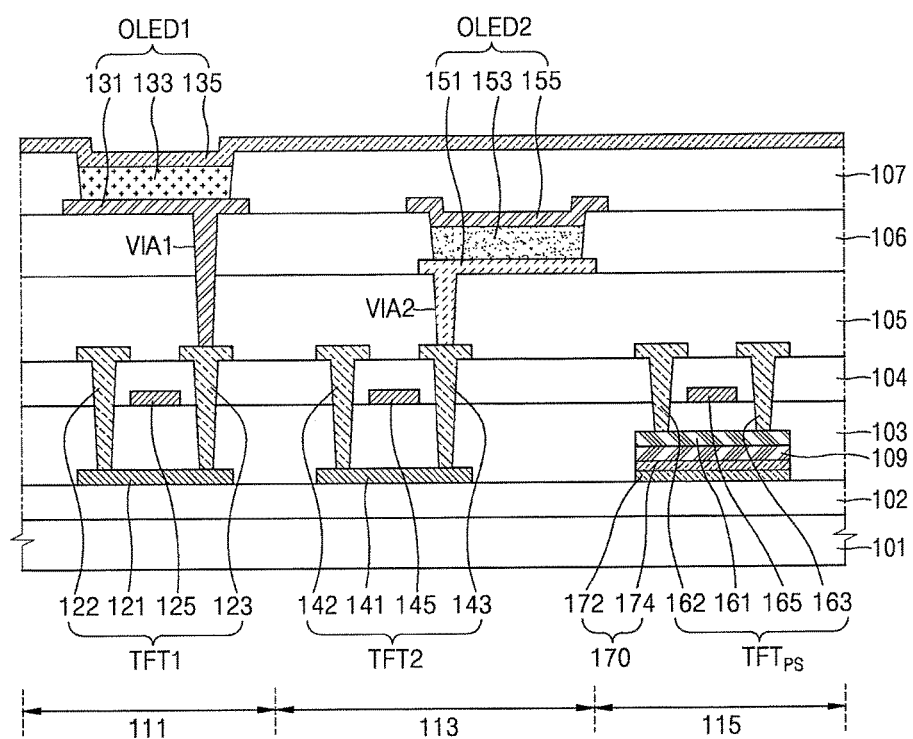
FIG. 9 illustrates another embodiment of a display panel.

FIG. 9 illustrates another embodiment of a display panel. This embodiment is the same as the embodiment in FIG. 4, except for the location of the light shielding member 170. Referring to FIG. 9, the first pixel PX1, the second pixel PX2, and the sensor unit SU may be arranged on the display area of the substrate 101. The first pixel PX1 includes the first pixel circuit and the first light-emitting device OLED1 connected to the first pixel circuit. The first pixel circuit may include first thin film transistor TFT1.

The first thin film transistor TFT1 includes the first semiconductor layer 121, the first source electrode 122, the first drain electrode 123, and the first gate electrode 125. The first light-emitting device OLED1 includes the first electrode 131, the second electrode 135, and the first intermediate layer 133 between the first electrode 131 and the second electrode 135. The first intermediate layer 133 includes the first emission layer. The first emission layer may emit light of a visible light wavelength band in a direction opposite to the substrate 101.

The second pixel PX2 includes the second pixel circuit and the second light-emitting device OLED2 connected to the second pixel circuit. The second pixel circuit may include the second thin film transistor TFT2. The second thin film transistor TFT2 includes the second semiconductor layer 141, the second source electrode 142, the second drain electrode 143, and the second gate electrode 145. The second light-emitting device OLED2 includes the first electrode 151, the second electrode 155, and the second intermediate layer 153 between the first electrode 151 and the second electrode 155. The second intermediate layer 153 includes the second emission layer. The second emission layer may emit light of an IR wavelength band in a direction of the substrate 101.

The second light-emitting device OLED2 may be arranged below (or at a layer below) the first light-emitting device OLED1. For example, at least the second emission layer 153 of the second light-emitting device OLED2 may be below the first emission layer 133 of the first light-emitting device OLED1.

The second light-emitting device OLED2, arranged below the first light-emitting device OLED1, may be spaced apart from the first light-emitting device OLED1 by a certain distance in a horizontal direction. Thus, the second light-emitting device OLED2 and the first light-emitting device OLED1 do not overlap each other. As a result, signal interference and/or color interference between the first light-emitting device OLED1 and the second light-emitting device OLED2 may be reduced or minimized.

The sensor unit SU may include the sensing thin film transistor TFTps. The sensor unit SU may include the switching transistor TRsw. The switching transistor TRsw may have, for example, the same structure as the first thin film transistor TFT1 of the first pixel PX1 or the second thin film transistor TFT2 of the second pixel PX2.

The sensing thin film transistor TFTps includes the third semiconductor layer 161, the third source electrode 162, the third drain electrode 163, and the third gate electrode 165. The third semiconductor layer 161 is a light-receiving layer which includes a semiconductor material sensitive to IR light. For example, the third semiconductor layer 161 may include a-SiGe.

The insulating layer 109 and the light shielding member 170 may overlap each other in a vertical direction, below the third semiconductor layer 161. The insulating layer 109 may include an inorganic material, e.g., $SiN_x$ or $SiO_x$. The insulating layer 109 may be a portion of the first insulating layer 103. The buffer layer 102 may be below the insulating layer 109 and the light shielding member 170. For example, both of the third semiconductor layer 161 and the light shielding member 170 may be arranged on the buffer layer 102.

The light shielding member 170 may include, for example, at least one of an organic material including a black pigment, e.g., a-Si, a-SiGe, and a-Ge. For example, the light shielding member 170 may include a stack of the first light shielding layer 172 including a-Ge and the second light shielding layer 174 including a-SiGe on the first light shielding layer 172.

The third semiconductor layer 161, the insulating layer 109, and the light shielding member 170 may be simultaneously formed. Thus, their side etch surfaces may correspond to one another. The light shielding member 170 may have the same size as the third semiconductor layer 161.

In the embodiment of FIG. 9, the third semiconductor layer 161 and the light shielding member 170 may be formed by performing a mask process once. Thus, the number of processes and the expense of making the display panel may be reduced compared to the embodiment of FIG. 4, in which the third semiconductor layer 161 is formed by performing the mask process twice.

Figure 10A:
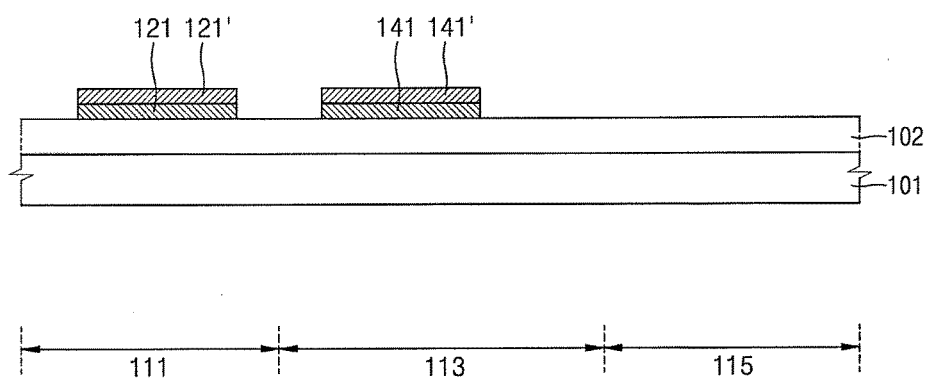
FIGS. 10A to 10I illustrate another embodiment of a method for manufacturing a display panel.

FIGS. 10A to 10I illustrate another embodiment of a method for manufacturing the display panel, which, for example, may be the display panel in FIG. 9. Referring to FIG. 10A, the first semiconductor layer 121 and the second semiconductor layer 141 may be formed on the substrate 101. The substrate 101 may include various materials, e.g., glass, metal, or plastic. According to an embodiment, the substrate 101 may include a substrate including a flexible material. The substrate 101 may include the first area 111 in which the first pixel PX1 is formed, the second area 113 in which the second pixel PX2 is formed, and the third area 115 in which the sensor unit SU is formed.

The buffer layer 102 may be formed throughout the substrate 101. The buffer layer 102 may be formed as a single layer or multiple layers including an inorganic material, e.g., $SiN_x$ and/or $SiO_x$.

A semiconductor layer may be formed on the buffer layer 102 using a semiconductor material and patterned by a photomask process to form the first semiconductor layer 121 of the first area 111 and the second semiconductor layer 141 of the second area 113. The first semiconductor layer 121 and the second semiconductor layer 141 may include the same material, e.g., an inorganic semiconductor material such as a-Si or poly-Si. Poly-Si, formed by crystallizing a-Si.

After a dry etching process for patterning the first semiconductor layer 121 and the second semiconductor layer 141, a strip process may be omitted. Thus, the photosensitive layers 121' and 141' may remain on patterns of the first semiconductor layer 121 and the second semiconductor layer 141. The photosensitive layers 121' and 141' may protect the first semiconductor layer 121 and the second semiconductor layer 141 from a dry etching process for patterning the third semiconductor layer 161.

Figure 10B:
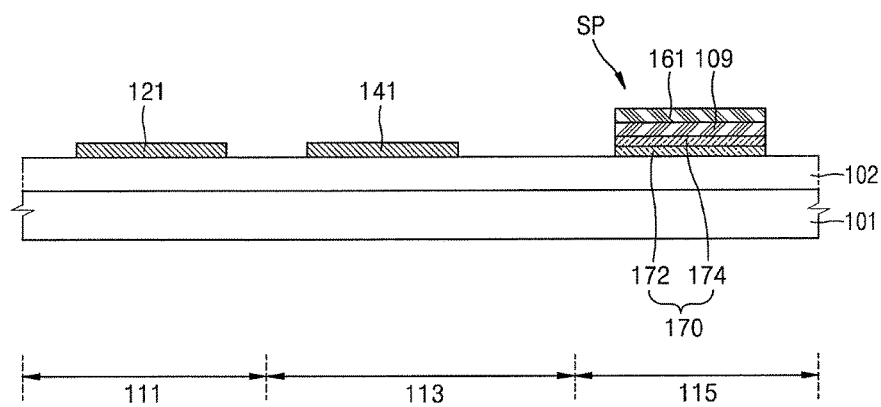

Referring to FIG. 10B, the third semiconductor layer 161 and the light shielding member 170 of the third area 115 may be formed on the buffer layer 102. After a first light shielding material layer, a second light shielding material layer, an insulating material layer, and a semiconductor layer are stacked on the buffer layer 102, the first light shielding material layer, the second light shielding material layer, the insulating material layer, and the semiconductor layer are simultaneously etched and patterned by a photomask process.

Accordingly, a pattern SP including the first light shielding layer 172, the second light shielding layer 174, the insulating layer 109, and the third semiconductor layer 161 may be formed. This, etch surfaces of the first light shielding layer 172, the second light shielding layer 174, the insulating layer 109, and the third semiconductor layer 161 may correspond to one another.

The first light shielding layer 172 may include a-Ge and the second light shielding layer 174 may include a-SiGe. The third semiconductor layer 161 may include a-SiGe and the insulating layer 109 may include an inorganic material, e.g., $SiN_x$ or $SiO_x$.

After the dry etching process for forming the pattern SP, the photosensitive layers 121' and 141' on the first and second semiconductor layers 121 and 141 and a photosensitive layer on the third semiconductor layer 161 may be removed by a strip process. (Processes described hereinafter may be the same as those illustrated with reference to FIGS. 7D through 7J, except where noted).

Figure 10C:
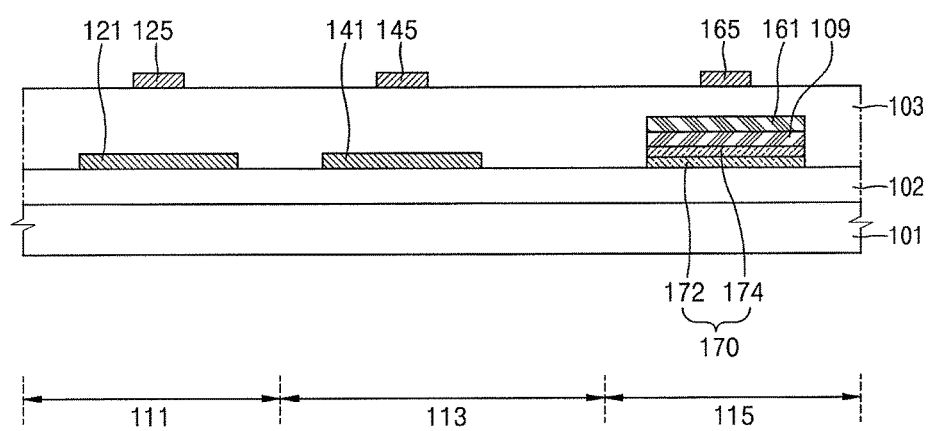

Referring to FIG. 10C, the first insulating layer 103 may be formed on the substrate 101 on which the first through third semiconductor layers 121, 141, and 161 are formed. The first through third gate electrodes 125, 145, and 165 may be formed on the first insulating layer 103.

Figure 10D:
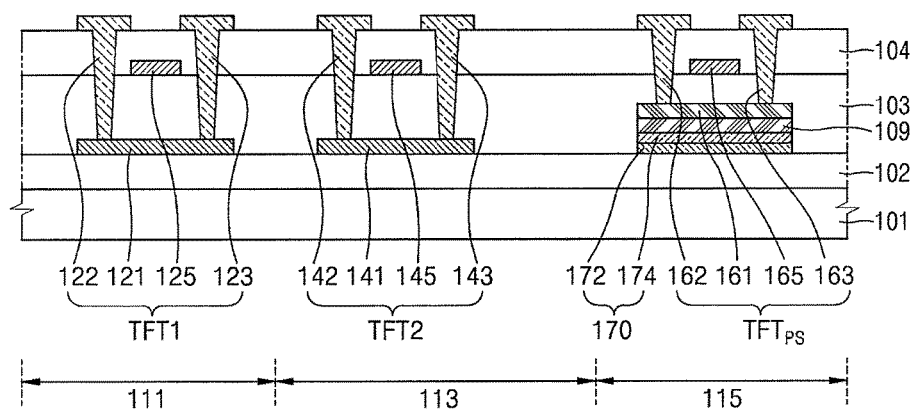

Referring to FIG. 10D, the second insulating layer 104 may be formed on the substrate 101 on which the first through third gate electrodes 125, 145, and 165 are formed. Also, contact holes exposing portions of the first through third semiconductor layers 121, 141, and 161 may be formed in the first insulating layer 103 and the second insulating layer 104. Next, the first through third source electrodes 122, 142, and 162 and the first through third drain electrodes 123, 143, and 163 may be formed on the second insulating layer 104.

Figure 10E:
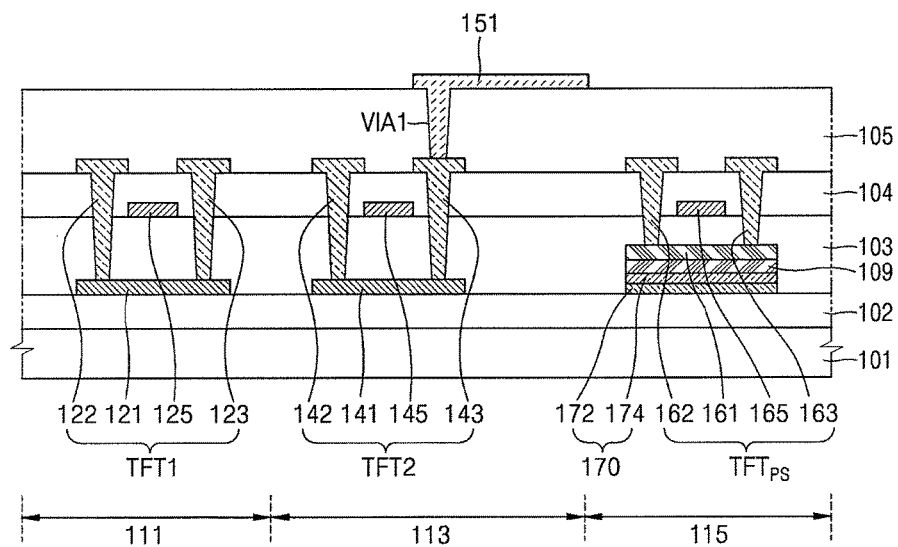

Referring to FIG. 10E, the third insulating layer 105 may be formed on the substrate 101 on which the thin film transistors are formed. The first via hole VIAL exposing a portion of the second source electrode 142 or the second drain electrode 143 (the second drain electrode in the case of FIG. 10E) may be formed in the third insulating layer 105. Then, the first electrode 151 of the second light-emitting device OLED2 may be formed on the third insulating layer 105. The first electrode 151 of the second light-emitting device OLED2 may be electrically connected to the second drain electrode 143 via the first via hole VIA1.

Figure 10F:
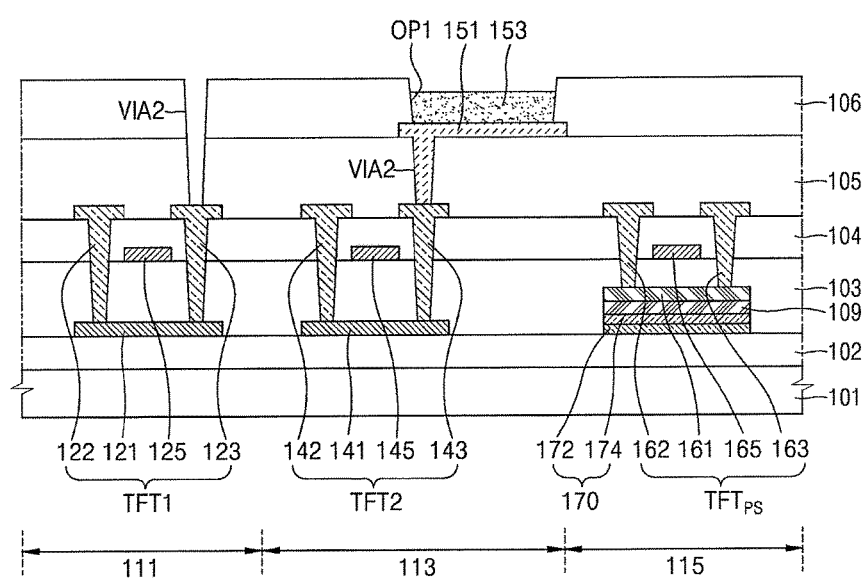

Referring to FIG. 10F, the fourth insulating layer 106 may be formed on the substrate 101 on which the first electrode 151 of the second light-emitting device OLED2 is formed. The first opening OP1 exposing a portion of the first electrode 151, and the second via hole VIA2 exposing a portion of the first source electrode 122 or the first drain electrode 123 (the first drain electrode in the case of FIG. 10F) of the first area 111, may be formed in the fourth insulating layer 106.

Also, the second intermediate layer 153 including the second emission layer may be formed on the first electrode 151 in the first opening OP1 of the second light-emitting device OLED2. The second emission layer may emit light of in an IR range.

Figure 10G:
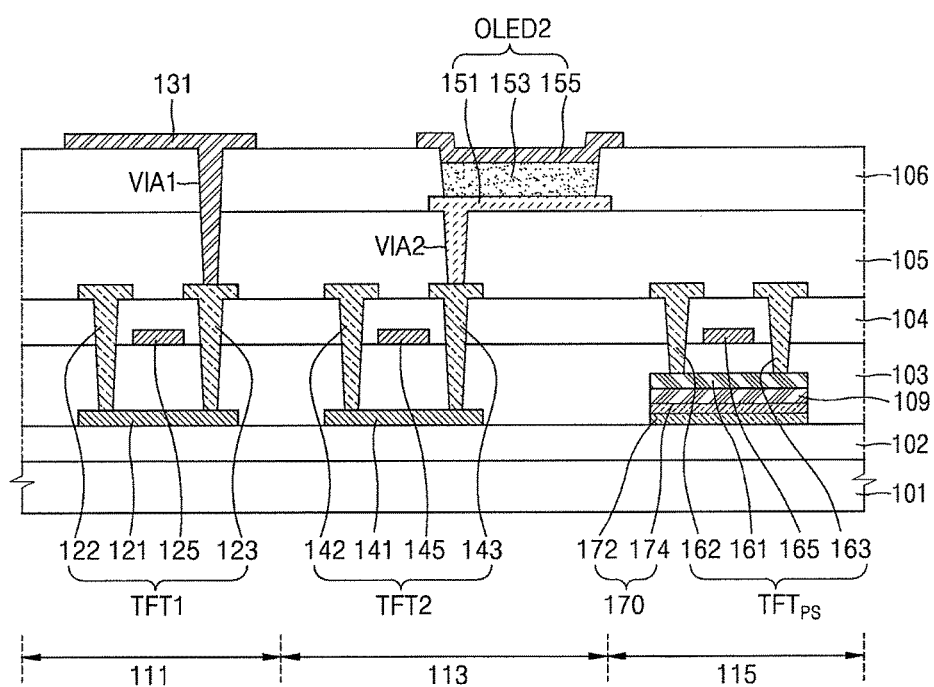

Referring to FIG. 10G, the first electrode 131 of the first light-emitting device OLED1 and the second electrode 155 of the second light-emitting device OLED2 may be formed on the substrate 101, on which the fourth insulating layer 106 and the second intermediate layer 153 are formed. The first electrode 131 of the first light-emitting device OLED1 may be electrically connected to the first drain electrode 123 via the second via hole VIA2.

In the embodiment of FIG. 10G, the first electrode 131 of the first light-emitting device OLED1 and the second electrode 155 of the second light-emitting device OLED2 include the same material. In one embodiment, the first electrode 131 of the first light-emitting device OLED1 and the second electrode 155 of the second light-emitting device OLED2 may be manufactured by separate processes using different materials.

Figure 10H:
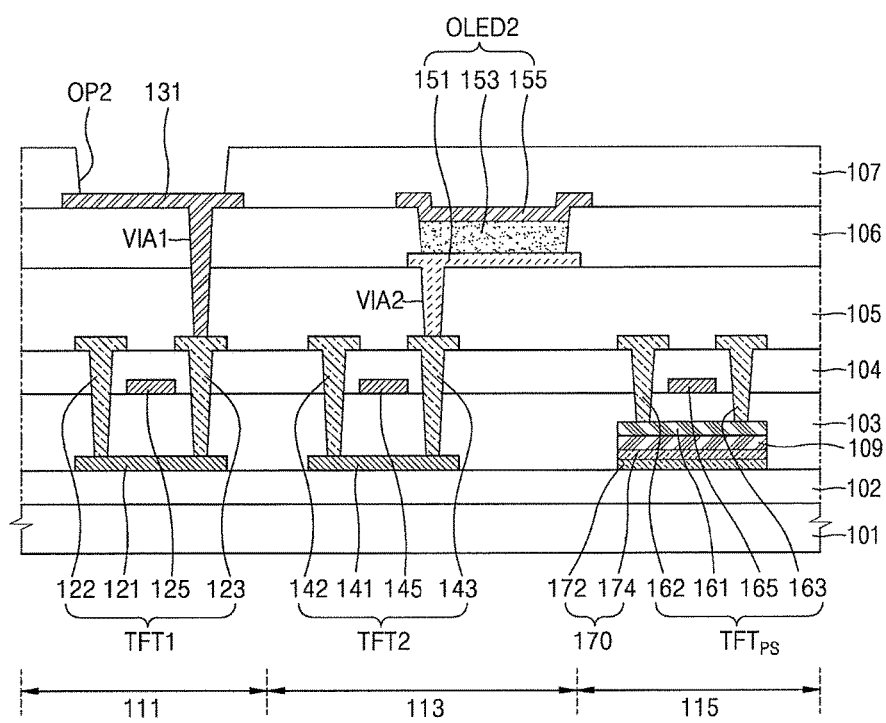

Referring to FIG. 10H, the fifth insulating layer 107 may be formed on the substrate 101 on which the first electrode 131 of the first light-emitting device OLED1 and the second light-emitting device OLED2 are formed. The second opening OP2 exposing a portion of the first electrode 131 of the first light-emitting device OLED1 may be formed in the fifth insulating layer 107.

Figure 10I:
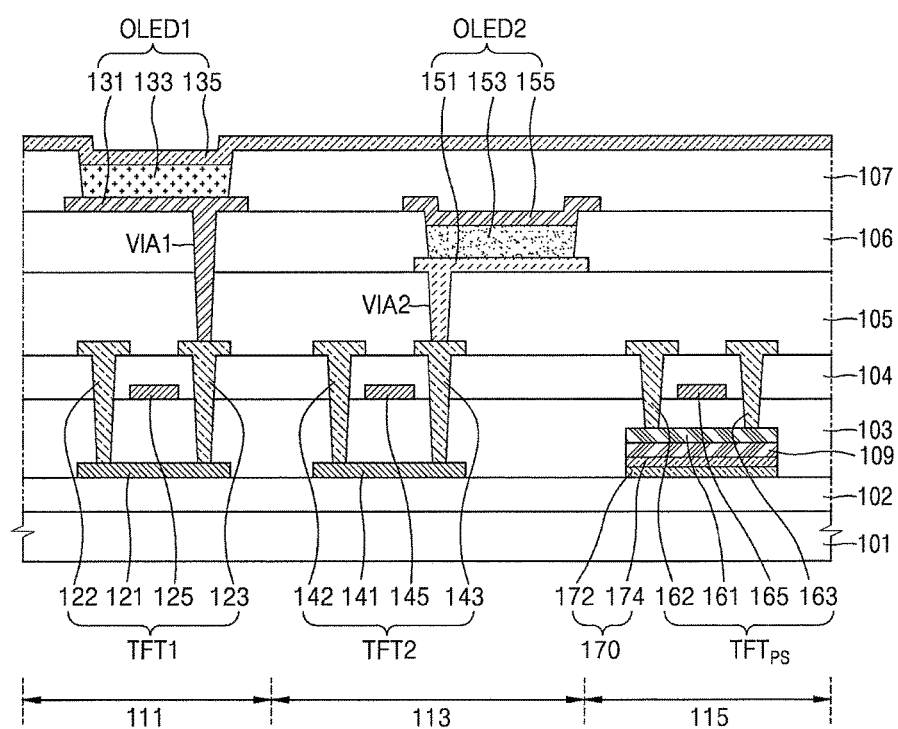

Referring to FIG. 10I, the first intermediate layer 133 including the first emission layer and the second electrode 135 may be formed on the first electrode 131 in the second opening OP2 of the first light-emitting device OLED1. The second electrode 135 of the first light-emitting device OLED1 may be formed throughout the substrate 101. The first emission layer may emit light in a visible light range.

Figure 11:
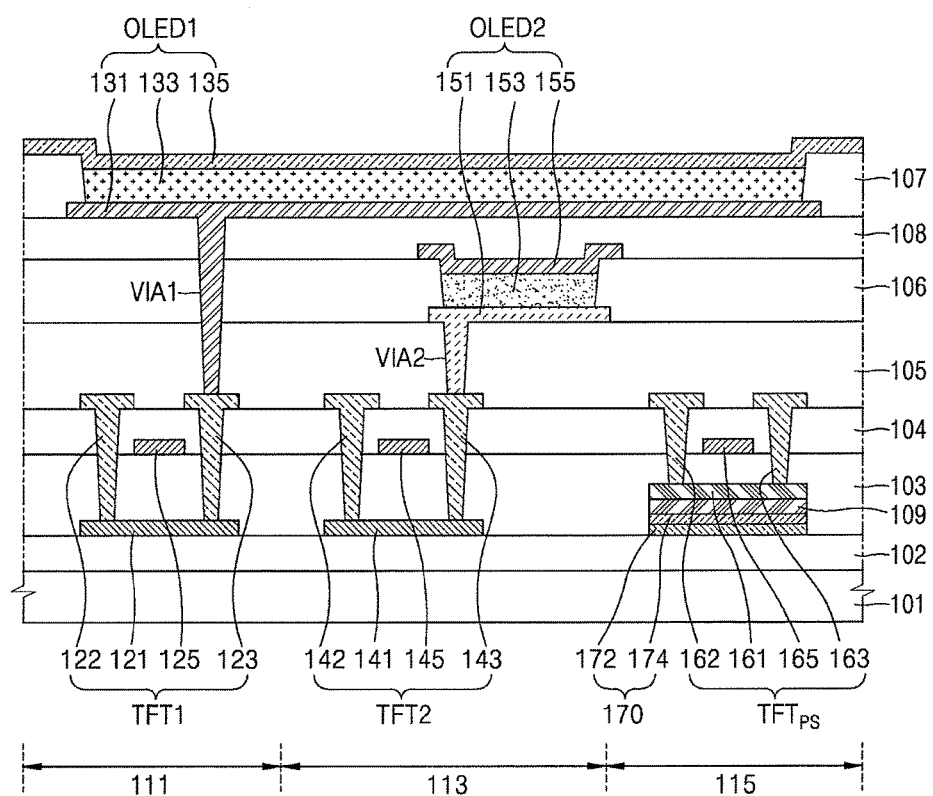
FIG. 11 illustrates another embodiment of a display panel.

FIG. 11 illustrates another embodiment of a display panel, which may differ from the embodiment in FIG. 9 in that the sixth insulating layer 108 is included between the first light-emitting device OLED1 of the first pixel PX1 and the second light-emitting device OLED2 of the second pixel PX2.

The second light-emitting device OLED2 of the second pixel PX2 may be arranged below (or at a layer below) the first light-emitting device OLED1 of the first pixel PX1. For example, at least the second emission layer 153 of the second light-emitting device OLED2 may be below the first emission layer 133 of the first light-emitting device OLED1.

The first light-emitting device OLED1 of the first pixel PX1 and the second light-emitting device OLED2 of the second pixel PX2 may at least partially overlap each other in a vertical direction as seen from a cross-sectional point of view. The second light-emitting device OLED2 arranged below the first light-emitting device OLED1 may at least partially overlap the first light-emitting device OLED1 in the vertical direction. When the first light-emitting device OLED1 of the first pixel PX1 and the second light-emitting device OLED2 of the second pixel PX2 at least partially overlap each other, aperture ratios of the first pixel PX1 and the second pixel PX2 may increase. The first pixel PX1 may be greater than the second pixel PX2.

In order to reduce or minimize signal interference and/or color interference between the first light-emitting device OLED1 and the second light-emitting device OLED2, the sixth insulating layer 108 may be included between the first light-emitting device OLED1 and the second light-emitting device OLED2. The sixth insulating layer 108 may be formed as a single layer or multiple layers including an organic material or an inorganic material, like the second insulating layer 104. Alternatively, sixth insulating layer 108 may be formed by alternating an organic material and an inorganic material.

In one embodiment, the second light-emitting device OLED2, which is below the sixth insulating layer 108, may be spaced apart from a side surface of the light-emitting device OLED1. Thus, the second light-emitting device OLED2 is below the first light-emitting device OLED1, and the second light-emitting device OLED2 does not overlap the first light-emitting device OLED1.

FIGS. 12 to 15 illustrate additional embodiments of a method for manufacturing a display panel. The embodiment in FIG. 12 may be like the embodiment in FIG. 4, except that the first pixel circuit of the first pixel PX1 and the second pixel circuit of the second pixel PX2 are not included and only the first light-emitting device OLED1 of the first pixel PX1 and the second light-emitting device OLED2 of the second pixel PX2 are included.

Figure 13:
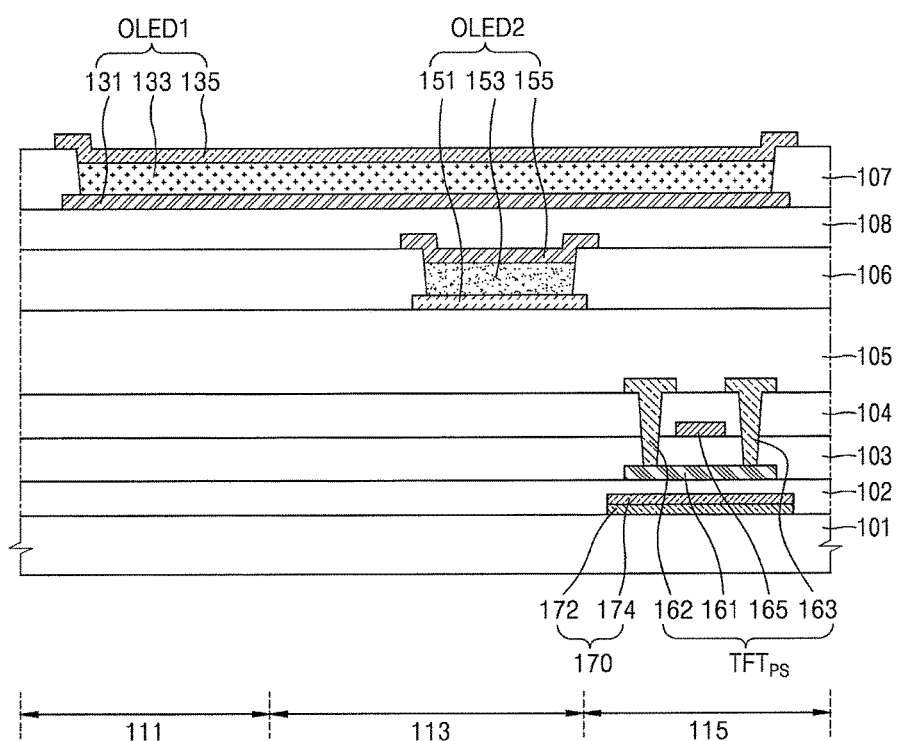

The embodiment in FIG. 13 may be like the embodiment in FIG. 8, except that the first pixel circuit of the first pixel PX1 and the second pixel circuit of the second pixel PX2 are not included and only the first light-emitting device OLED1 of the first pixel PX1 and the second light-emitting device OLED2 of the second pixel PX2 are included.

Figure 14:
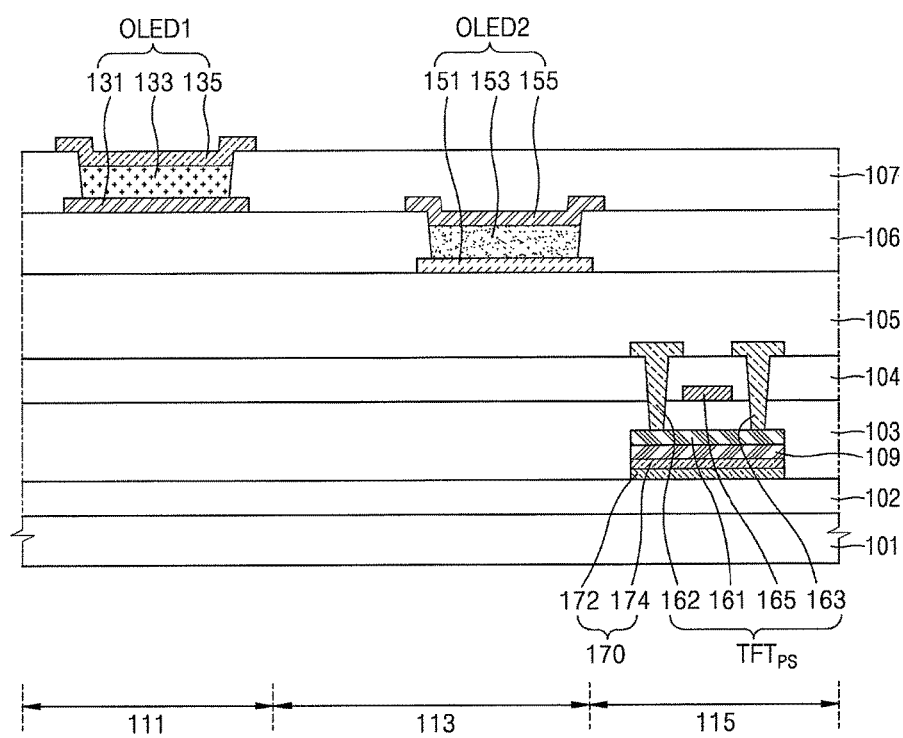

The embodiment in FIG. 14 may be like the embodiment in FIG. 9, except that the first pixel circuit of the first pixel PX1 and the second pixel circuit of the second pixel PX2 are not included and only the first light-emitting device OLED1 of the first pixel PX1 and the second light-emitting device OLED2 of the second pixel PX2 are included.

Figure 15:
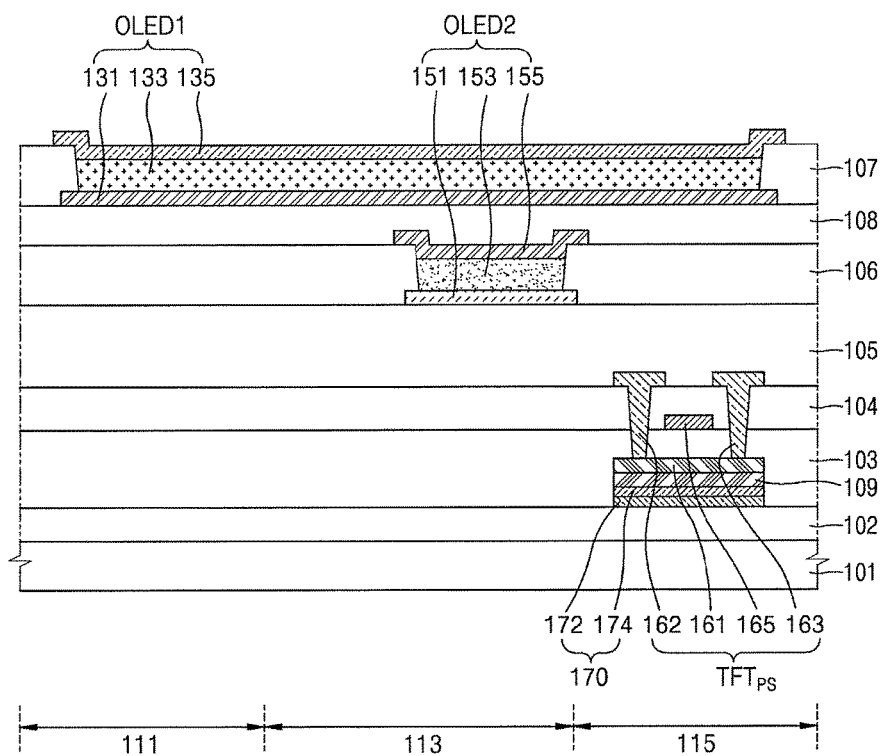

The embodiment in FIG. 15 may be like the embodiment in FIG. 11, except that the first pixel circuit of the first pixel PX1 and the second pixel circuit of the second pixel PX2 are not included and only the first light-emitting device OLED1 of the first pixel PX1 and the second light-emitting device OLED2 of the second pixel PX2 are included.

In the embodiments of FIGS. 12 to 15, the first light-emitting device OLED1 of the first pixel PX1 includes first electrode 131, the second electrode 135, and the first intermediate layer 133 between the first electrode 131 and the second electrode 135. The first intermediate layer 133 includes the first emission layer. The first emission layer may emit light in a visible wavelength band in a direction opposite to the substrate 101 based on a voltage applied to the first electrode 131 and the second electrode 135.

The second light-emitting device OLED2 of the second pixel PX2 includes the first electrode 151, the second electrode 155, and the second intermediate layer 153 between the first electrode 151 and the second electrode 155. The second intermediate layer 153 includes the second emission layer. The second emission layer may emit light of in an IR wavelength band in a direction of the substrate 101 based on a voltage applied to the first electrode 151 and the second electrode 155.

In the embodiments of FIGS. 12 to 15, as seen from a cross-sectional point of view, the second light-emitting device OLED2 of the second pixel PX2 is located below the first light-emitting device OLED1 of the first pixel PX1. For example, the first emission layer 133 of the first light-emitting device OLED1 is at least below the second emission layer 153 of the second light-emitting device OLED2.

Accordingly, signal and/or light interference between the light-emitting devices emitting light of different bands may be reduced.

Figure 12:
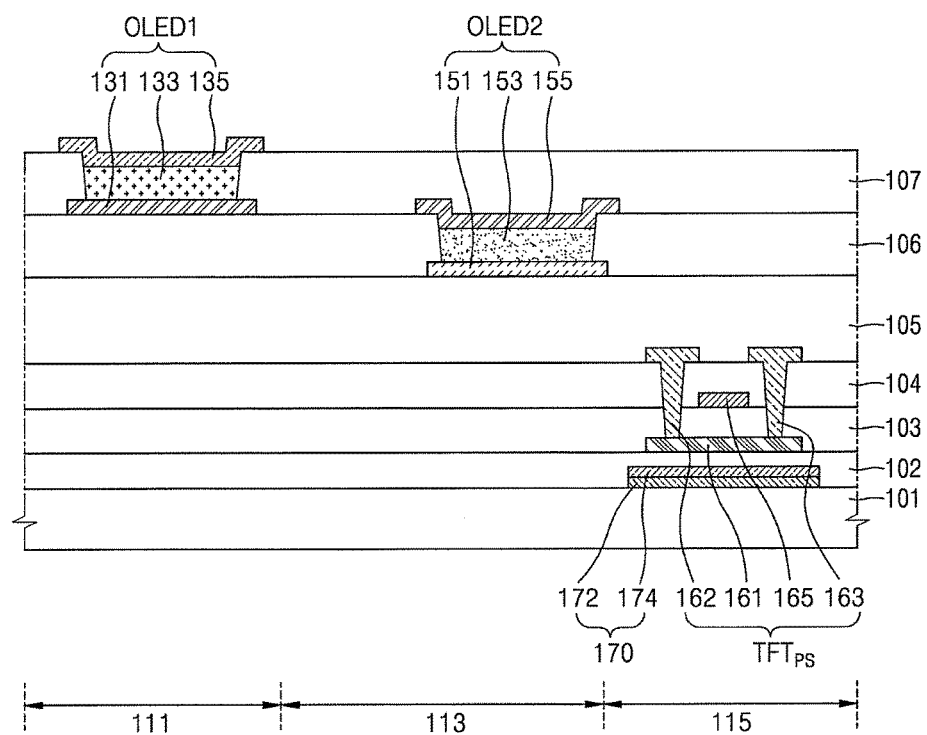
FIGS. 12 to 15 illustrate additional embodiments of a display panel.

In the embodiments of FIGS. 12 and 14, the second light-emitting device OLED2 of the second pixel PX2 may be located below the first light-emitting device OLED1 of the first pixel PX1 and be spaced apart from a side surface of the first light-emitting device OLED1. The first electrode 131 of the first light-emitting device OLED1 and the second electrode 155 of the second light-emitting device OLED2 may be on the same insulating layer (e.g., the fourth insulating layer 106).

In the embodiments of FIGS. 13 and 15, the second light-emitting device OLED2 of the second pixel PX2 may be located below the first light-emitting device OLED1 of the first pixel PX1 and may at least partially overlap the first light-emitting device OLED1. The first electrode 131 of the first light-emitting device OLED1 and the second electrode 155 of the second light-emitting device OLED2 may be provided with an insulating layer (e.g., the sixth insulating layer 108) therebetween.

In the embodiments of FIGS. 13 and 15, the first light-emitting device OLED1 and the second light-emitting device OLED2 overlap each other. In another embodiment, the first light-emitting device OLED1 and the second light-emitting device OLED2 may not overlap each other. For example, the second light-emitting device OLED2 may be below the first light-emitting device OLED1 and spaced apart from a side surface of the first light-emitting device OLED1 by a certain distance. Thus, the second light-emitting device OLED2 does not overlap the first light-emitting device OLED1.

In accordance with one or more of the aforementioned embodiments of the display apparatus, a display device, a light-emitting device, and a sensing device are appropriately arranged on a substrate. Thus, the light-emitting device and the biometric information sensing device do not need to be physically coupled to a rear surface of the substrate, separately from the display device. Accordingly, the display apparatus may be formed to be thin. Also, image displaying and biometric information sensing (e.g., fingerprint extraction, vein pattern extraction, iris pattern extraction, etc.) may simultaneously or separately performed.

A pattern in which one or more veins are arranged may be referred to as a vein pattern. Vein patterns may be different among individuals. Thus, a vein pattern may be sensed as biometric information for purposes of identifying individuals. The vein pattern has drawn attention as a new form of authentication. This is because a vein pattern constitutes unique body information and therefore is in no danger of being robbed. Also, a vein pattern does not leave traces like fingerprints. The thickness and size of a vein may vary according to the growth (or age) of a human, but the pattern does not change.

Oxidized hemoglobin including oxygen flows in an artery, while hemoglobin in which oxygen is reduced flows in a vein. Reduced hemoglobin absorbs light having a wavelength of about 760 nm, that is, NIR light. Thus, the sensor units SU may sense a lesser amount of NIR light in a location in which a vein exists, compared to other locations. Using this characteristic, the display apparatus of the aforementioned embodiments may extract the vein pattern.

The display apparatus of the aforementioned embodiments may be realized as a portable terminal, a flexible wearable device, etc. When a user contacts the display apparatus, the display apparatus may extract the vein pattern in a body in contact with or near to the display apparatus. In one embodiment, the display apparatus may pre-store the vein pattern of an authenticated user and may examine whether the user that contacted the display apparatus is the authenticated user, based on a comparison of the extracted vein pattern and the pre-stored vein pattern.

Thus, in accordance with one or more of the aforementioned embodiments, the display apparatus may be thin and have large areas, while integrally including a light source and a light sensing device.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. Accordingly, it will be understood by those of skill in the art that various changes in form and details may be made without departing from the spirit and scope of the embodiments set forth in the claims.

What is claimed is:

1. A display apparatus, comprising:
   a substrate;
   a first pixel on the substrate, the first pixel including a first light-emitting diode, the first light-emitting diode including a first electrode, a second electrode, and a first emission layer between the first and second electrodes, the first emission layer to emit light in a first wavelength band, the first electrode of the first light-emitting diode to reflect the light of the first emission layer in a first direction;
   a second pixel on the substrate, the second pixel including a second light-emitting diode, the second light-emitting diode including a third electrode, a fourth electrode, and a second emission layer between the third and fourth electrodes, the second emission layer to emit light in a second wavelength band, the fourth electrode of the second light-emitting diode to reflect the light of the second emission layer in a second direction opposite to the first direction, the second emission layer of the second light-emitting diode below the first emission layer of the first light-emitting diode;
   a light sensor on the substrate to sense the light in the second wavelength band emitted from the second pixel and reflected by an object; and
   a light shield adjacent to the light sensor on the substrate, wherein
   the first electrode of the first light-emitting diode and the fourth electrode of the second light-emitting diode are adjacent to each other in a horizontal direction.

2. The display apparatus as claimed in claim 1, wherein:
   the light sensor includes a thin film transistor, and
   the thin film transistor includes a third semiconductor layer.

3. The display apparatus as claimed in claim 2, wherein the third semiconductor layer includes amorphous silicon germanium.

4. The display apparatus as claimed in claim 2, further comprising:
   an insulating layer between the light shield and the third semiconductor layer.

5. The display apparatus as claimed in claim 4, wherein the insulating layer includes at least one of silicon nitride or silicon oxide.

6. The display apparatus as claimed in claim 1, wherein the light shield has a stack structure including:
   a first light shielding layer including amorphous germanium, and
   a second light shielding layer including amorphous silicon germanium.

7. The display apparatus as claimed in claim 1, wherein:
   the first electrode of the first light-emitting diode is reflective and the second electrode of the first light-emitting diode is transparent, and
   the third electrode of the second light-emitting diode is transparent and the fourth electrode of the second light-emitting diode is reflective.

8. The display apparatus as claimed in claim 1, wherein the fourth electrode of the second light-emitting diode is on a same layer as the first electrode of the first light-emitting diode.

9. The display apparatus as claimed in claim 1, further comprising:
   an insulating layer between the fourth electrode of the second light-emitting diode and the first electrode of the first light-emitting diode.

10. The display apparatus as claimed in claim 1, wherein:
    the first pixel includes a first thin film transistor electrically connected to the first light-emitting diode and including a first semiconductor layer, and
    the second pixel includes a second thin film transistor electrically connected to the second light-emitting diode and including a second semiconductor layer.

11. The display apparatus as claimed in claim 10, wherein each of the first semiconductor layer and the second semiconductor layer includes polysilicon.

12. The display apparatus as claimed in claim 1, wherein a resolution of the second pixel is lower than a resolution of the first pixel.

13. The display apparatus as claimed in claim 1, wherein:
    the first wavelength band includes a visible light range, and
    the second wavelength band includes an infrared range.

14. A method of manufacturing a display apparatus, the method comprising:
    preparing a substrate;
    forming, on the substrate, a light sensor to sense light of a second wavelength band reflected by an object;
    forming a second light-emitting diode, the second light-emitting diode including a third electrode, a fourth electrode, and a second emission layer between the third and fourth electrodes, the second emission layer to emit the light of the second wavelength band, the fourth electrode of the second light-emitting diode to reflect the light of the second emission layer in a direction to the substrate;
    forming a first light-emitting diode, the first light-emitting diode including a first electrode, a second electrode, and a first emission layer between the first and second electrodes, the first emission layer to emit light of a first wavelength band, the first electrode of the first light-emitting diode to reflect the light of the first emission layer in a direction opposite to the substrate; and
    forming a light shield in a path of light incident to the light sensor, wherein the first electrode of the first light-emitting diode and the fourth electrode of the second light-emitting diode are formed concurrently.

15. The method as claimed in claim 14, wherein the first electrode of the first light-emitting diode and the fourth electrode of the second light-emitting diode are substantially coplanar.

16. The method as claimed in claim 14, wherein forming the light shield includes:
    before forming the light sensor, stacking a first light shielding layer and a second light shielding layer on the substrate and patterning the first light shielding layer and the second light shielding layer.

17. The method as claimed in claim 14, wherein:
    forming the light shield is performed during forming of the light sensor, and
    forming the light sensor includes stacking a first light shielding layer, a second light shielding layer, an insulating layer, and a semiconductor layer on the substrate and patterning the first light shielding layer, the second light shielding layer, the insulating layer, and the semiconductor layer,
    the first light shielding layer and the second light shielding layer are included in the light shield, and
    the semiconductor layer is included in the light sensor.

18. The method as claimed in claim 14, further comprising:
    before forming the first light-emitting diode and the second light-emitting diode, forming a first thin film transistor electrically connected to the first light-emitting diode and a second thin film transistor electrically connected to the second light-emitting diode.

19. The method as claimed in claim 14, wherein:
    the first wavelength band includes a visible light range, and
    the second wavelength band includes an IR range.

20. An apparatus, comprising:
    a first pixel to emit a first light in a first wavelength band to display an image, the first pixel including a first light-emitting diode having a first electrode, a second electrode, and a first emission layer between the first and second electrodes, the first emission layer to emit the first light, the first electrode of the first light-emitting diode to reflect the first light in a first direction;
    a second pixel to emit a second light in a second wavelength band to detect an object, the second pixel including a second light-emitting diode having a third electrode and a fourth electrode, and a second emission layer between the third and fourth electrodes, the second emission layer to emit the second light, the fourth electrode of the second light-emitting diode to reflect the second light in a second direction opposite to the first direction, and
    a sensor to sense the second light in the second wavelength band different from the first wavelength band, wherein the second light in the second wavelength band is indicative of biometric information of the object and the image corresponds to the biometric information, wherein
    the first electrode of the first light-emitting diode and the fourth electrode of the second light-emitting diode are adjacent to each other in a horizontal direction.

21. The apparatus as claimed in claim 20,
    wherein the sensor is to receive the second light in the second wavelength band as reflected from the object that is indicative of the biometric information.

22. The apparatus as claimed in claim 21, wherein:
    the object is a body part, and
    the biometric information includes a vein pattern in the body part.

23. The apparatus as claimed in claim 21, further comprising:
    a substrate, wherein the first pixel emits the first light in the first wavelength band from a first surface of the substrate and the second pixel emits the second light in the second wavelength band from a second surface of the substrate opposite to the first surface.

24. The apparatus as claimed in claim 23, wherein the first pixel, the second pixel, and the sensor are at different levels from the substrate.

* * * * *